US009440006B2

(12) United States Patent
Van Boxtel

(10) Patent No.: US 9,440,006 B2
(45) Date of Patent: Sep. 13, 2016

(54) POROUS TISSUE SCAFFOLDS

(71) Applicant: FUJIFILM Corporation, Minato-Ku, Tokyo (JP)

(72) Inventor: Huibert Van Boxtel, Tilburg (NL)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/271,079

(22) Filed: May 6, 2014

(65) Prior Publication Data
US 2014/0329992 A1   Nov. 6, 2014

Related U.S. Application Data

(63) Continuation of application No. PCT/GB2012/052703, filed on Oct. 31, 2012.

(30) Foreign Application Priority Data

Nov. 7, 2011 (GB) .................................. 1119173.1

(51) Int. Cl.
| A61K 38/39 | (2006.01) |
| A61L 27/22 | (2006.01) |
| A61L 27/56 | (2006.01) |
| A61C 8/00  | (2006.01) |
| A61K 38/00 | (2006.01) |

(52) U.S. Cl.
CPC .............. *A61L 27/56* (2013.01); *A61C 8/0016* (2013.01); *A61L 27/222* (2013.01); *A61L 27/227* (2013.01)

(58) Field of Classification Search
None
See application file for complete search history.

(56) References Cited

U.S. PATENT DOCUMENTS

| 5,880,240 A * | 3/1999 | Tsuno ................... C08F 212/36 521/147 |
| 6,447,701 B1 | 9/2002 | Heschel et al. |
| 2004/0028738 A1 | 2/2004 | Huang et al. |
| 2012/0308612 A1* | 12/2012 | De ....................... A61K 9/0019 424/400 |
| 2013/0004549 A1 | 1/2013 | Nakamura et al. |

FOREIGN PATENT DOCUMENTS

| CN | 1380114 | 11/2002 |
| CN | 101066469 | 11/2007 |
| EP | 0926543 | 6/1999 |
| EP | 1273615 | 1/2003 |
| EP | 1566186 | 8/2005 |
| EP | 1860142 | 11/2007 |
| WO | 03007789 | 1/2003 |
| WO | 2009156760 | 12/2009 |
| WO | 2011108537 | 9/2011 |

OTHER PUBLICATIONS

Szarko et al. (2010) Freeze-thaw treatment effects on the dynamic mechanical properties of articular cartilage, BMC Musculoskelet Disord, vol. 11, 231 (total 8 pages).*
Annabi et al. (2010) Controlling the Porosity and Microarchitecture of Hydrogels for Tissue EngineeringTissue Eng., vol. 16, No. 4, pp. 371-383.*
Suetsugu et al. (2007) Structural and Tissue Reaction Properties of Novel Hydroxyapatite Ceramics with Unidirectional Pores, Trans Tech Public., vols. 330-332, pp. 1003-1006.*
Mikos et al., "Preparation and characterization of poly(L-lactic acid) foams", Polymer, 35(5):1068-1077 (1994).
Harris et al., "Open pore biodegradable matrices formed with gas foaming", J. Biomed. Mater. Res., 42:396-402 (1998).
Shugens et al., "Polylactide macroporous biodegradable implants for cell transplantation. II. Preparation of polylactide foams by liquid-liquid phase separation", J. Biomed. Mater. Res., 30:449-461 (1996).
Whang et al., "A novel method to fabricate bioabsorbable scaffolds", Polymer, 36(4):837-842 (1995).
Wegst et sl., "Biomaterials by freeze casting", Phil., Trans. R. Soc. A, 368:2099-2122 (2010).
International Search Report for PCT/GB2012/052703 dated Feb. 6, 2013, with Written Opinion.
International Preliminary Report on Patentability for PCT/GB2012/052703 dated May 22, 2014.
Wu et al., "Preparation of aligned porous gelatin scaffolds by unidirectional freeze-drying method", Acta Biomaterialia, 6(3):1167-1177 (2010).
Search Report for GB1119173.1 dated Feb. 29, 2012.
Madaghiele et al., "Collagen-based matrices with axially oriented pores", J. Biomed. Mater. Res., Part A, 85(3):757-767 (2008).
Communication dated Jan. 27, 2015 from the Japanese Patent Office in counterpart Application No. 2014-539398.
Notification of First Office Action for Chinese Application No. 201280054603.9 dated Dec. 29, 2014.

* cited by examiner

*Primary Examiner* — Manjunath Rao
*Assistant Examiner* — Samuel Liu
(74) *Attorney, Agent, or Firm* — Sughrue Mion, PLLC

(57) ABSTRACT

A method for forming a porous tissue material.

18 Claims, 27 Drawing Sheets

POROUS TISSUE SCAFFOLDS

FIELD OF INVENTION

The present invention relates to methods for producing porous materials, especially porous tissue scaffolds with a distinct pore geometry, from solutions of biocompatible polymers and to biocompatible articles produced from these scaffolds.

BACKGROUND OF THE INVENTION

Biomaterials are designed to replace injured or diseased tissue. Ideally, they are scaffolds for tissue regeneration with properties similar to those of the healthy tissue that they replace. Designed to cover a two-dimensional surface or to fill a three-dimensional void, they should, in parallel to healing, gradually be absorbed so that, ultimately, the site of injury becomes almost indistinguishable from the surrounding tissue. To achieve these goals, the biomaterial must fulfil several design requirements: it has to possess a sufficiently large porosity, its surface chemistry and topography must be suited for cell adhesion, proliferation and differentiation; it needs to possess an appropriate architecture to guide tissue regeneration; and it should allow for controlled absorption when the scaffold is no longer required. Additionally, the scaffold must, despite a high overall porosity that considerably weakens its mechanical properties, possess sufficient stiffness, strength and toughness to perform the natural tissue's function while the wound is healing. The currently available tissue scaffolds comprise different unabsorbable biocompatible polymers such as polyethylene terephthalate; fluorinated polymers, such as polytetrafluoroethylene (PTFE) and fibres of expanded PTFE; and polyurethanes. Some available tissue scaffolds do comprise absorbable polymers such as poly-lactic acid, hyaluronic acid, collagen and gelatin. However, their pore geometry ranges are not optimal.

Typical methods for preparing such three-dimensional porous polymer scaffolds include: a solvent-casting and particle-leaching technique comprising mixing a polymer with single-crystal salt particles, drying the mixture and then immersing the dried material to leach the salt particles (A. G. Mikos et al., Polymer, 35, 1068 (1994)); a gas forming technique comprising expanding a polymer with $CO_2$ gas (L. D. Harris et al., J. Biomed. Mater. Res., 42, 396 (1998)); a thermally induced phase separation technique including immersing a polymer-containing solvent in a non-solvent to make the polymer porous (C. Schugens, et al., J. Biomed. Mater. Res., 30, 449 (1996)); and a freeze-drying method comprising dissolving a polymer in a solvent to prepare a polymer solution and then freeze-drying the polymer solution with liquid nitrogen (K. Whang, Polymer, 36, 837 (1995). A specialized form of thermal induced phase separation, also referred to as directional freeze casting, has obtained the most defined porous tissue scaffolds thus far and is extensively described in the literature (Wegst et al Phil. Trans. R. Soc. A 2010, 368 p. 2099-2122). This method depends on the controlled solidification of a solvent, such as water, in a dispersion which results in the directional phase separation between solvent and the dispersed material due to directional growth of solid solvent crystals. After removal of the solvent (e.g. freeze-drying) a porous material remains. This method allows some control of the geometry of the material by controlling the speed at which the freeze front travels through the dispersed material. The tissue scaffold materials Remaix and OptiMaix comprising animal derived natural collagen and elastin are prepared using a freeze casting method, which is described in U.S. Pat. No. 6,447,701.

However, for many applications it is preferable that the material be highly uniform (e.g. the material density, pore size and pore orientation or mechanical properties should be have a limited variation throughout the material). The current biocompatible polymer porous tissue scaffolds lack sufficient uniformity. In addition, preferred custom-made biocompatible polymers with enhanced properties for cell attachment and growth are designed to be completely and molecularly soluble in an aqueous solvent or solvent mixture. Furthermore, it is usually desirable that these biocompatible polymers be highly purified and freed from soluble and insoluble (particulate) impurities. The use of such a molecularly dissolved biocompatible polymer improves the homogeneity of the resulting porous scaffold. The object of the current invention is to provide a process by which highly uniform biocompatible polymer tissue scaffolds, comprising biocompatible polymers, and articles prepared with these tissue scaffolds may be prepared.

SUMMARY OF THE INVENTION

The present invention provides a method for producing a porous material from a liquid solution comprising a biocompatible polymer the method comprising:
a. introducing the biocompatible polymer solution into a thermally insulated container with a thermally conducting surface;
b. optionally allowing at least part of the biocompatible polymer solution to gel, by cooling the container in a cooling device to a temperature in the range of from sample melting point (Tm) to 25° C.;
c. freezing the biocompatible polymer gel/solution in a controlled fashion via the thermally conducting surface by:
   (i) rapidly dropping the temperature of the cooling device to between about −10° C. and about −50° C., within no more than 5 minutes, so as to form a thin layer of frozen biocompatible polymer gel/solution on the thermally conducting surface;
   (ii) rapidly raising the temperature of the cooling device, within no more than 5 minutes, to a temperature closer to but still below the Tm;
   (iii) gradually lowering the temperature of the cooling device so as to induce a constant unidirectional growth rate of ice-crystals in the biocompatible polymer gel/solution, initiated from the frozen layer formed in step c (i); and
d. freeze-drying the product of step c (iii).

Preferably the porous material produced by the method of the present invention is a porous tissue scaffold.

Tm, the aqueous sample melting point, is usually close to 0° C. but upon addition of some organic solvents or salts it may significantly deviate from 0° C. If organic solvents and/or salts are added to the sample, resulting in a lowering of Tm, the sample melting point can be in the range of between 0 and −10° C., but most of the time the Tm is in the range of between 0 and −5° C.

The porous tissue material produced by this method has a uniform porous structure where the average equivalent circular diameter (ECD) is in the range of from between about 10 to about 1000 microns, depending on targeted cell type and tissue type and location, with a small ECD standard deviation ($ECD_{SD}$). Typical values obtained by the current invention for $ECD_{SD}$ are in the range of 60 to 20% of the ECD value. Preferred $ECD_{SD}$ values are 40% or less. It is also preferred that the porous material prepared by this method has an average ECD of the columnar porous structure in the range of from between about 10 to about 1000 microns and preferably in the range of from about 100 to 500 microns The porous tissue material produced by the method of the invention has an improved uniformity with respect to its material density, pore size and pore orientation over the materials described in the prior-art. This renders it particularly suitable for use in porous tissue scaffolds and biocompatible articles.

GENERAL DEFINITIONS

The term "comprising" is to be interpreted as specifying the presence of the stated parts, steps or components, but does not exclude the presence of one or more additional parts, steps or components.

Reference to an element by the indefinite article "a" or "an" does not exclude the possibility that more than one of the element(s) is present, unless the context clearly requires that there be one and only one of the elements. The indefinite article "a" or "an" thus usually means "at least one".

Term 'porous tissue scaffold' and 'porous scaffold' are used interchangeably and are to be interpreted as used herein as a three dimensional molecular matrix of biocompatible polymers which acts as a microenvironment to which tissue cells are attracted and can attach.

Biocompatible polymers as used herein means any artificial or natural biodegradable or non-degradable polymer such as, for example, but not limited to; collagen, gelatin, chitosan, carrageenan, alginate, hyaluronic acid, dextran, poly(lactic acid), poly(glycolic acid) (PGA), poly(lactic-co-glycolic acid) (PLGA), poly(.epsilon.-carprolactone), poly(anhydrides), polyorthoesters, poly(vinyl alcohol), poly(ethylene glycol), polyurethane, poly(acrylic acid), poly(N-isopropyl acrylamide), poly(ethylene oxide)-poly(propylene oxide)-poly(ethylene oxide) copolymer(Pluronic™), a copolymer thereof, or a mixture thereof.

The term "uniform" and "uniformity" as used herein is to be interpreted as a limited variation of parameters such as, but not limited to pore-size, the (elliptic) circular diameter, pore-shape, the range of observed angles between individual directed pores, the straightness of pores and the mechanical properties such as but not limited to rigidness, brittleness, compressibility.

The term "columnar pore" as used herein is to be interpreted as a pore geometry of the pore lumen that approximates a cylinder or elliptic cylinder in which a cylinder is defined as a body the surface of which is formed by the points at a fixed distance from a given line segment, the axis of the cylinder. The solid enclosed by this surface and by two planes perpendicular to the axis is also called a cylinder. An elliptic cylinder is a cylinder whose directrix is an ellipse. A cross section perpendicular to the longitudinal columnar pore direction as used herein can have an irregular shape with a roundness of 0.5 or more. In one embodiment the roundness error is 40 or less.

The term roundness, (R), provides a measure of the circularity of a pore. A perfect circle has a roundness of 1. R is calculated from the area of the pore (A), and the maximum diameter (dmax) according to the formula:

$$R = \frac{4A}{\pi d\max^2}$$

The term Equivalent Circle Diameter (ECD) is defined as the area of an irregularly shaped pore, A, which can be expressed in terms of an ECD. The correspondence between the ECD and the actual diameter of a pore obviously improves with increasing roundness of pores. The ECD is given by the formula:

$$ECD = \frac{\left(\frac{4A}{\pi}\right)1}{2}$$

The average ECD, was determined by counting the pore pixels for each individual pore in a given fixed surface area and deriving each individual pore ECD by a simple mathematical transformation. Then the average ECD and the $ECD_{SD}$ are determined. These parameters are determined in a cross-sectional image taken perpendicularly to the longitudinal pore direction.

For further details on these and other parameters describing the shape, form and distribution of pores in biocompatible scaffold materials seethe ASTM Standard Guide for Interpreting Images of polymeric Tissue Scaffolds, Designation: F2603-06. A definition of "ECD" may also be found in this standard.

The term "cylindrical pore diameter" as used herein is to be interpreted as the average pore ECD, determined by counting the pore pixels for each individual pore in a given fixed surface area and deriving each individual pore ECD by a simple mathematical transformation. Then the average ECD and the $ECD_{SD}$ are determined. These parameters are determined in a cross-section image taken perpendicularly to the longitudinal pore direction.

The term "in-vitro culturing system" as used herein is to be interpreted as any kit, apparatus or compounds used for the growth of cells, tissues, organs or parts of organs ex-vivo.

The term "biocompatible article" as used herein is to be interpreted as any material used for the treatment of a medical condition or for a cosmetic correction where the material is placed on or in the body of a human or animal and which do not evoke an adverse immunologic response. This includes materials which may degrade and be absorbed by the body over time. This material can be in any form such as, but not limited to: bandages, powders, sponges, hemostats, and sutures, implants of any kind, injectable particles, microspheres, microcarriers, gels or putties.

As used herein, "pluripotent," "pluripotency," "pluripotent cells" and equivalent expressions refer to cells that are capable of both proliferation and self-renewal in cell culture and differentiation towards a variety of cell populations that include those that exhibit multipotent properties, for example, pluripotent ES cells can give rise to each of the three embryonic cell lineages. Pluripotent cells, however, cannot give rise to extra-embryonic tissues such as the amnion, chorion, and other components of the placenta, and may not be capable of producing an entire organism, i.e. pluripotent cells are not "totipotent". Pluripotency can be demonstrated by providing evidence of stable developmental potential, to form derivatives of all three embryonic germ layers from the progeny of a single cell and to generate a teratoma after injection into an immuno-suppressed mouse. Other indications of pluripotency include expression of genes known to be expressed in pluripotent cells and, characteristic morphology. The pluripotent cells of the present invention can be derived using any method known to those skilled in the art. "Pluripotent cells" include but are not limited to stem cells, induced pluripotent cell (iPS cell) such as an induced pluripotent stem cell (iPSC), e.g., a human induced pluripotent stem cell (hiPSC), or a human embryonic stem cell (hESC), parthenogenic cells and the like.

"Totipotent" as used herein, refers to the ability of a cell to develop into all types of cells, including extraembryonic tissues (e.g. placenta) and to give rise to an entire organism (e.g. a mouse or human).

"Self-renewal" refers to the ability of a stem cell to divide and form more stem cells with properties identical to the parent stem cell, thereby allowing the population of stem cells to be replenished indefinitely.

The term "particle" as used herein is to be interpreted as any particle of solid matter of any shape irregular or discrete with a "smallest dimension size" of at least 20 to 50 nm this includes microspheres, any type of granules, any type of fibers or filaments.

The term "particle free" as used herein means that the solution is essentially free of particles of a size greater than 50 nm and preferably it is free of particles of a size greater than 20 nm. The size of any particles may be determined by electron microscopic inspection or laser light scattering techniques, dynamic (PCS) or static (SLS). The presence of particles can be detected by means of various independent methods, such as elemental mapping (EDAX) of sample cross-sections to observe locally enhanced densities of specific elements, or (optical or electron) microscopic inspection of sample cross-sections to detect embedded particles, or using specific enzymes (e.g. trypsin for collagens or gelatins) to hydrolyse the sample polymer network until completion and using light scattering techniques to detect particles.

The term "freeze-casting" and "thermally induced phase separation" are used interchangeably and refer to methods that create porous structures by solidifying a solvent within a solution, sol-gel or dispersion by lowering the temperature of the solution, dispersion or sol-gel in such a way that the solvent separates from the dissolved and dispersed materials. By removing the solidified solvent by a second process a porous structure of the dissolved material remains. By controlling how the temperature change dissipates throughout the dispersion, solution or sol-gel the geometry of the pores can be adjusted. When the temperature gradient is applied in one direction (also called the freeze front travel direction) it is known as 'unidirectional freeze-casting'

The term "perpendicular" as used herein is to be interpreted as a line or plane which forms an angle of about 80 to 110 degrees with another line or plane.

The terms "protein" or "polypeptide" or "peptide" are used interchangeably and refer to molecules consisting of a chain of amino acids, without reference to a specific mode of action, size, three-dimensional structure or origin.

"Gelatin" and "gelatin-like" as used herein refers to any gelatin, whether extracted by traditional methods or recombinant or biosynthetic in origin, or to any molecule having at least one structural and/or functional characteristic of gelatin. The term encompasses both the composition of more than one polypeptide included in a gelatin product, as well as an individual polypeptide contributing to the gelatin material. Thus, the term gelatin as used in reference to the present invention encompasses both a gelatin material comprising gelatin polypeptides, as well as an individual gelatin polypeptide. Polypeptides from which gelatin can be derived are polypeptides such as collagens, procollagens, and other polypeptides having at least one structural and/or functional characteristic of collagen. Such a polypeptide could include a single collagen chain, or a collagen homotrimer or heterotrimer, or any fragments, derivatives, oligomers, polymers, or subunits thereof, containing at least one collagenous domain (Gly-Xaa-Yaa region, where Xaa and Yaa are independently any amino acid). The term specifically contemplates engineered sequences not found in nature, such as altered collagen sequences, e.g. a sequence that is altered, through deletions, additions, substitutions, or other changes, from a naturally occurring collagen sequence. Such sequences may be obtained from, for example, suitable altered collagen polynucleotide constructs as described in EP0926543, EP1014176, WO01/34646, WO04/085473, EP1894945, WO08/103,041, WO08/103,044, WO08/103, 043 and also specifically the examples of EP0926543 and EP1014176 which are hereby incorporated by reference.

A "cross-linking agent" as described herein refers to a composition comprising a cross-linker. "Cross-linker" as used herein refers to a reactive chemical compound that is able to introduce covalent intra- and intermolecular chemical bonds in organic molecules.

DETAILED DESCRIPTION OF THE INVENTION

It was surprisingly found that by using a novel three steps process during a freeze-casting procedure, it is possible to prepare porous tissue scaffolds that are more uniform with respect to having a consistent columnar pore size throughout the porous scaffold material, than previously described porous scaffold materials. This process is carried out in a container that is thermally conductive on at least one of its sides. The process essentially provides using an ultra low chilling temperature to quickly cool and freeze a small part of the whole sample to create a thin frozen sample layer over the whole area of one side of the container. This thin frozen layer subsequently acts as a template ice site for the growth of columnar ice-crystals in the subsequent steps of the process. The presence of this thin densely frozen layer provides more uniform and better control of the subsequent growth of columnar ice crystals and therefore better control of the size, form and number density of the pore cavities left in the biocompatible polymer material. The thickness of this layer can be minimized by optimising the thermal properties and geometry of the freezing container design and the chilling and heating rate in steps c (i) and c(ii). Usual thickness values are from 0.1 to 1.5 mm, depending also on the type of biocompatible polymer and its concentration.

Freezing/temperature control may be achieved using any suitable cooling device which would be known to a person skilled in the art. Preferably the cooling device is a chill bath.

The invention will now be described with reference to FIGS. 1 and 2.

Figure 1:
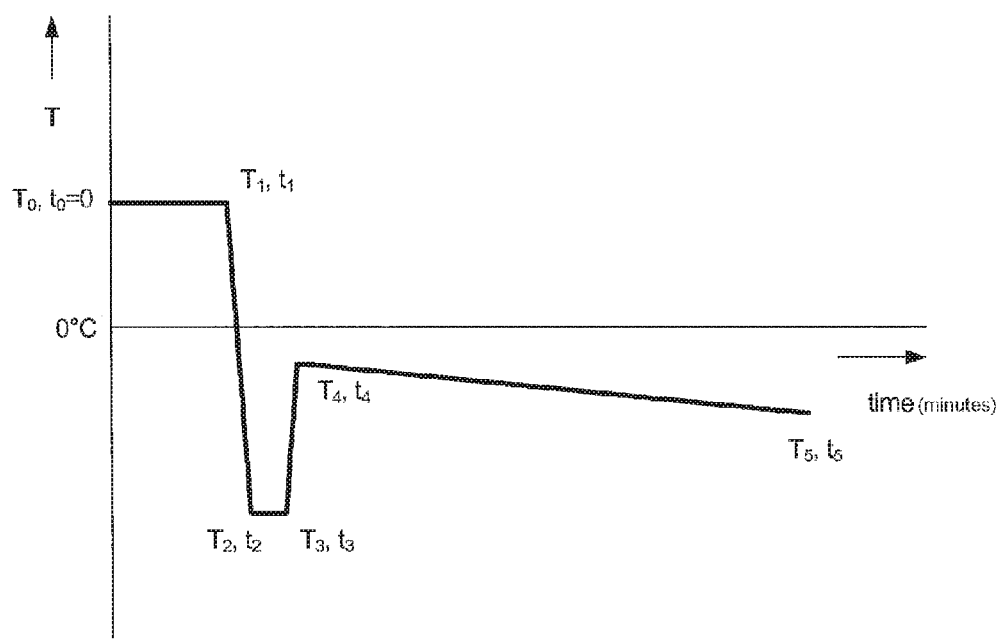
FIG. 1 shows the temperature/time profile for producing a porous material from a biocompatible polymer according to the invention.
Figure 2:
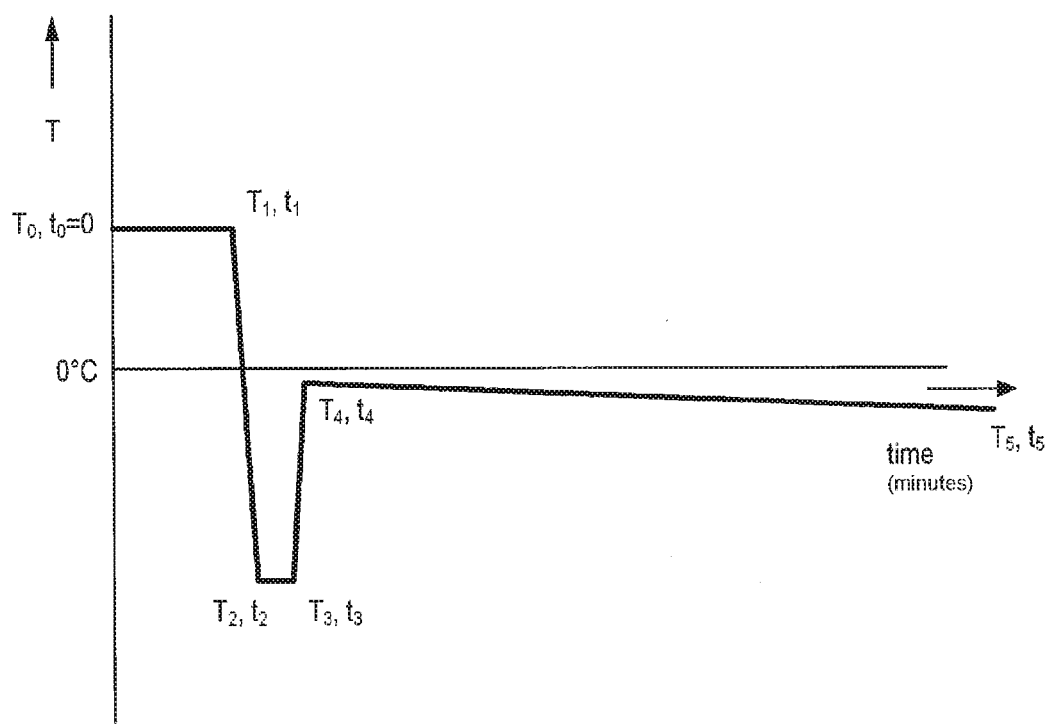
FIG. 2 shows the temperature/time for producing a porous material from a biocompatible polymer according to the invention when smaller columnar pores are required.
Figure 3:
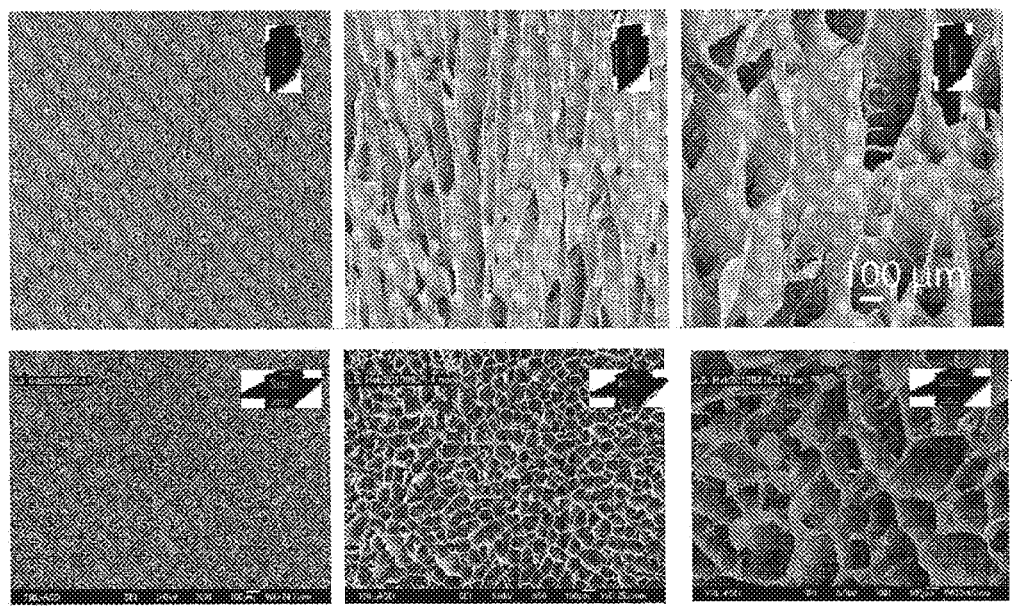
FIG. 3 shows scanning electron microscope (SEM) images of the range of columnar pore sizes which can be uniformly prepared with particle free recombinant gelatin solutions, using the method according the invention. The upper row are images of cross-sections cut laterally/vertically in the center sample part and the bottom row is cut transversally/horizontally 2~3 mm from the top down

FIGS. 1 and 2 show the biocompatible polymer solution being introduced into the thermally insulated container with a single thermally conducting surface in a chill bath ($T_0$, $t_0$). Additives such as ethanol, methanol or acetic acid or other non-toxic or other easily removable compounds can optionally be added to alter the average pore size of the final freeze-dried sample.

i. The biocompatible polymer solution is cooled and at least a fraction of it forms a gel (1 volume percent or more with the gel typically occupying the volume closest to the chilled surface) ($T_1$, $t_1$).

The temperature is then rapidly dropped.

ii. The chill bath is cooled within 5 minutes ($t_2$–$t_1$) to a temperature ($T_2$) and the biocompatible polymer gel/solution is allowed to form a thin layer of frozen biocompatible polymer solution at the thermally conductive side of the container ($T_3$, $t_3$).

iii. The chill bath temperature is then rapidly raised to temperature ($T_4$) within 5 minutes ($t_4$–$t_3$) wherein $T_4$ is closer to Tm than $T_2$ but still below it.

iv. A slow and gradual ramped temperature drop time ($t_5$–$t_4$) of at least 5 minutes from $T_4$ to $T_5$ wherein $T_5$ is lower than $T_4$ to induce a columnar growth of ice-crystals in the biocompatible polymer solution or gel, initiated by the already frozen layer of biocompatible polymer solution which is perpendicular to the thermally conductive side of the container.

The temperature parameters $T_0$, $T_1$, $T_2$, $T_3$, $T_4$ and $T_5$ and the time parameters, $t_1$ $t_2$, $t_3$, $t_4$, and $t_5$, to obtain a targeted pore structure and average ECD need to be optimized for each type and concentration of biocompatible polymer and for the presence of any additives. Furthermore the sample height requires optimization of the parameters $T_5$ and $t_5$ with respect to $T_4$ and $t_4$. Higher samples will require a longer duration of slow temperature ramping from $T_4$ to $T_5$ to complete the freezing process.

The columnar pores formed in the porous material using the method of the present invention have superior uniformity and symmetry in comparison the materials previously described. Preferably the material which corresponds to the thin frozen layer formed in step c i, which has no columnar pores, is removed. This dense bottom layer typically measures 0.1 to 2 mm thickness but, if desired, can be reduced to less than 1 mm by optimizing the chill bath temperature profile. Specifically the parameters $t_2$–$t_1$, $T_2$, $t_3$–$t_2$, $T_3$, $T_4$ and $t_4$–$t_3$.

In one preferred embodiment the temperature $T_2$ is in the range of from about minus 10° C. to about minus 50° C. The chill bath temperature drop from $T_1$ to $T_2$ is preferably reached within 3 minutes and is more preferably reached in less than 2 minutes. The temperature profile for this temperature change may have any shape or form. This includes both linear and non linear profiles and may be optimized to achieve a specific uniform pore-size.

In a further preferred embodiment the temperature $T_4$ is about minus 4° C. but always above temperature $T_3$. The raise in temperature of the chill bath from $T_3$ to $T_4$ is preferably reached within 2 minutes and is more preferably reached in less than 1 minute. The temperature profile for this temperature change may have any shape or form. This includes both linear and non linear profiles and can be optimized to achieve a specific uniform average pore-size.

The temperature profile $T_4$ to $T_5$ may have any shape or form. This includes both linear and non linear profiles and may be optimized to achieve a specific uniform pore-size.

In general the lower $T_4$ is set and the greater the slope of the temperature drop $T_4$ to $T_5$ the smaller the pore size.

The thermally insulated container can have any shape or form and can be made from any suitable material. The thermally conductive surface may be made from any suitable thermally conductive material such as, for example, metals like copper and aluminum and include thermally conductive ceramics and polymers.

Preferably the thermally insulated container is PTFE or a teflon-like plastic, optionally in combination with a foamed material such as polyurethane or a ceramic foam, and the thermally conductive surface is a metal, particularly good thermal conductors like aluminum or copper.

Preferably the container is cylindrical, elliptic cylindrical or rounded rectangular, the sides and optionally the top-side of which are thermally insulated.

In step d any suitable freeze drying methods known in the art may be used.

Preferably after freeze drying the material which corresponds to the thin dense layer formed in step c (i), and which has no columnar pores, is removed.

Preferably the porous material formed by the method of the present invention comprises a porous material comprising a biocompatible polymer that is substantially free of particles, with one symmetrical uniform columnar porous structure and an average pore ECD between about 10 to 1000 microns. More preferably the average pore ECD is between about 50 (preferably 100) to 500 microns.

Preferably the biocompatible polymer solution is degassed before use. This can be performed by any technique known in the art. Preferably the biocompatible polymer solution is degassed by lowering the atmospheric pressure below 50 mbar for at least 10 minutes.

It is also preferred that the biocompatible polymer solution is essentially particle free. By using essentially particle free molecular solutions of biocompatible polymers it is possible to prepare porous tissue scaffolds which are not only more uniform with respect to having a consistent columnar pore size throughout the porous scaffold material, than previously described porous scaffold materials, but also more uniform with respect to material density, because of the lack of particles, In the prior art suspension or dispersions of materials are used to prepare porous scaffolds (Kuberka et al. 2002 Int J Artif Organs 20(1):67-73; Wegst et al. Phil. Trans. R. Soc. A 2010, 368 p. 2099-2122; Meghri et al. 2010 JOM 62(7): 71-75 and U.S. Pat. No. 6,447,701). The inventor has found that the particles in these materials lead to variances in not only material density but also in the symmetry and pore size of the columnar pores. This second effect is thought to be the result of the particles acting as nucleation sites for ice-formation during the freeze-casting process. In the present invention the lack of such particles decreases the nucleation temperature of the sample gel/solution. This is shown by the fact that the formation of ice in molecular solutions of biocompatible polymers happens at a lower temperature than for systems containing particles. Typical nucleation temperatures in particle free biocompatible polymer solutions are between −8 and −30° C., whereas Schoof et al, 2001, J Biomed Mater Res 58(4): 352-357) shows that collagen suspensions freeze just under 0° C. Because of this lower temperature the subsequent growth of the formed ice-crystals in molecular solutions of biocompatible polymers is more sudden and less controllable than in systems containing particles. The inventor of the present invention has however surprisingly found that this problem can be circumvented by using the novel three steps process of the invention during the freeze-casting procedure.

It is also preferred that the biocompatible polymer solution is filter sterilized before use preferably through a 0.45 micron filter and more preferably through a 0.2 micron filter.

Preferably after freeze drying (in step d) the porous material is cross-linked.

Preferably the process of the present invention is used to prepare porous tissue scaffold material and in this case the freeze dried material from step d is preferably cross-linked.

Cross-linking may utilize any cross-linking agent and technique known to one skilled in the art.

In one preferred embodiment the porous material is cross-linked by a process which comprises chemical cross-linking. Suitable chemical cross-linking agents include: aldehydes or dialdehydes, such as formaldehyde and glutaraldehyde, carbodiimides, diisocyanates, diketones, such as diacetyl and chloropentanedion, bis(2-chloroethylurea), 2-hydroxy-4,6-dichloro-1,3,5-triazine, reactive halogen-containing compounds disclosed in U.S. Pat. No. 3,288,775, carbamoyl pyridinium compounds in which the pyridine ring carries a sulphate or an alkyl sulphate group disclosed in U.S. Pat. No. 4,063,952 and U.S. Pat. No. 5,529,892, divinylsulfones, and the like and S-triazine derivatives such as 2-hydroxy-4,6-dichloro-s-triazine. It also includes photoactivated cross-linking techniques.

Preferred chemical cross-linking agents are 1-ethyl-3-(3-dimethyl aminopropyl) carbodiimide (EDC) and hexamethylene diisocyanate (HMDIC).

In another preferred embodiment the porous material is cross-linked by a process which comprises dehydrothermal cross-linking.

In a preferred embodiment preferably, the biocompatible polymer is either a synthetic biodegradable polymer selected from the group consisting of poly glycolic acid (PGA), poly lactic acid (PLA), and poly(DL-lactic-co-glycolic acid) (PLGA), or a natural biodegradable polymer selected from the group consisting of chitosan, collagen, gelatin a copolymer thereof, or a mixture thereof. In an even more preferred embodiment the biocompatible polymer solution comprises a recombinant gelatin-like protein.

The use of recombinant gelatin-like proteins is of medical benefit in comparison to the conventionally produced gelatins from animal sources. There are safety issues with natural gelatins, such as the concern over potential immunogenic, e.g., antigenic and allergenic, responses. Also the inability to completely characterize, purify, or satisfactorily reproduce naturally derived gelatin mixtures is of ongoing concern in the pharmaceutical and medical communities. There are also additional safety concerns with respect to bacterial contamination and endotoxin loads resulting from the extraction and purification processes.

Recombinant technology allows the design of gelatin-like proteins with superior characteristics such as, for example, low immunogenicity, improved cell attachment and controlled biodegradability. EP0926543, EP1014176, WO01/34646, WO2004/085473, EP1894945, WO2008/103041, WO2008/103044, WO2008/103043 and also specifically the examples of EP 0926543 and EP 1014176, describe recombinant gelatins and their production methods, using methylotrophic yeasts, in particular *Pichia pastoris* recombinant gelatin-like proteins disclosed in these references are incorporated herein by reference.

It is preferred that the biocompatible polymer solution used in the method of the present invention comprises a recombinant gelatin-like protein which comprises at least one RGD motif. More preferably the biocompatible polymer solution comprises recombinant gelatin-like protein which is further enriched in RGD motifs. RGD-enriched gelatins in the context of this invention are described in WO2004/085473 and WO2008/103041 and the RGD-enriched gelatins disclosed therein are incorporated herein by reference.

Preferably in the recombinant gelatin-like protein the percentage of RGD motifs related to the total number of amino acids is at least 0.4% and if said recombinant gelatin-like protein comprises 350 amino acids or more, each stretch of 350 amino acids contains at least one RGD-motif.

More preferably in the recombinant gelatin-like protein the percentage of RGD-motifs related to the total number of amino acids is at least 0.6%, especially at least 0.8%, more especially at least 1.0%, particularly at least 1.2% and more particularly at least 1.5%.

In a further preferred embodiment the recombinant gelatin-like protein has a reduced level of hydroxyproline residues. Hydroxylation of proline is a requirement for the formation of triple helices in collagen which is an unfavorable characteristic for the porous scaffold material formed by the current invention as it leads to particulate aggregates and fibers or filaments of proteinacious material. Preferably in the recombinant gelatin-like protein less than 10%, more preferably less than 5% of the amino acid residues of the recombinant gelatin-like proteins are hydroxyprolines. It is especially preferred that the recombinant gelatin-like protein is free from hydroxyprolines. A further benefit described in WO 2002/070000 of recombinant gelatin-like proteins which are free from hydroxyprolines is that they do not show immune reactions involving IgE, in contrast to natural gelatin.

In a further preferred embodiment the gelatin-like proteins are functionalized for enhanced cell binding and/or with minimal immunogenicity such as, for example, those gelatin-like proteins disclosed in EP 1608681 and EP 1368056. Functionalized recombinant gelatin-like proteins can be designed to have improved cell-binding properties that stimulate cellular infiltration of tissues surrounding the medical device after implantation.

In another further embodiment the recombinant gelatin-like proteins used in the present invention are recombinant gelatin-like proteins with a calculated iso-electric point above 5, preferably a calculated iso-electric point above 6 and most preferably a calculated iso-electric point above 7.

In a further embodiment recombinant gelatin-like proteins used in the present invention have a molecular weight of at least 20 kDa, more preferably 25 kDa, especially of at least 35 kDa and more especially of at least 50 kDa.

It is preferred that the recombinant gelatin-like proteins used in the present invention have a molecular weight in the range of from 20 kDa to 75 kDa.

During the preparation of the porous material comprising gelatin-like protein more than one form of gelatin may be used.

When the method of the present invention is used to prepare a porous tissue scaffold material it is preferable that the gelatin used should be biodegradable and so not require invasive surgical methods for its removal after stimulation/tissue regeneration. Moreover biodegradability is another important stimulatory factor in the regeneration of tissue. A priori it is not obvious whether recombinant gelatins will be broken down by the same mechanisms causing degradation of natural gelatins. It is known that natural gelatins and collagens are degraded in the human body by proteases and more specifically matrix-metalloproteinases (MMP). Matrix metalloproteinases (MMP's) are zinc-dependent endopeptidases. The MMP's belong to a larger family of proteases known as the metzincin superfamily. Collectively they are capable of degrading all kinds of extracellular matrix proteins, but they can also process a number of bioactive molecules. An important group of MMP's are the collagenases. These MMP's are capable of degrading triple-helical fibrillar collagens into distinctive ¾ and ¼ fragments. These collagens are the major components of bone and cartilage, and MMP's are the only known mammalian enzymes capable of degrading them. Traditionally, the collagenases are: MMP-1 (interstitial collagenase), MMP-8 (neutrophil collagenase), MMP-13 (collagenase 3) and MMP-18 (collagenase 4). Another important group of MMP's is formed by the gelatinases. The main substrates of these MMP's are type IV collagen and gelatin, and these enzymes are distinguished by the presence of an additional domain inserted into the catalytic domain. This gelatin-binding region is positioned immediately before the zinc binding motif, and forms a separate folding unit which does not disrupt the structure of the catalytic domain. The two members of this sub-group are: MMP-2 (72 kDa gelatinase, gelatinase-A) and MMP-9 (92 kDa gelatinase, gelatinase-B). However, International patent application WO2008/103045 discloses that a recombinant gelatin that does not comprise a known cleavage site for MMP was enzymatically degradable by human matrix metalloproteinase 1 (MMP1). Apparently many more types of recombinant gelatin than predicted can be degraded. Therefore a porous tissue scaffold comprising recombinant gelatin will exhibit the required gradual biodegradation for a composition providing a cellular scaffold function at first instance which is gradually replaced by autologous extracellullar matrix as it degrades.

A preferred aspect of the invention provides a method for preparing a porous tissue scaffold material comprising a method comprising the following steps:

a. dissolution of the biocompatible polymer in a solvent or solvent mixture;

b. degassing of the biocompatible polymer solution;

c. introducing the biocompatible polymer solution into a thermally insulated container with a single thermally conducting surface, optionally adding additives;

d. optionally allowing at least part of the biocompatible polymer solution to gel by cooling the container to a temperature in the range of from sample Tm to 25° C.;

e. unidirectionally freezing the sample, with control of the freezing rate, by exposing the container to a cooling device which utilizes a temperature profile comprising at least three steps:

(i) rapidly dropping the temperature of the cooling device to between about −10° C. and about −50° C., within no more than 5 minutes, so as to form a thin layer of frozen biocompatible polymer gel/solution on the thermally conducting surface;

(ii) rapidly raising the temperature of the cooling device, within no more than 5 minutes, to a temperature closer to but still below sample Tm;

(iii) gradually lowering the temperature of the cooling device so as to induce a laminar growth of ice-crystals in the biocompatible polymer gel/solution, initiated from the frozen layer formed in step e (i);

f. freeze drying the material obtained in step e at reduced pressure;

g. optionally removing the material which corresponds to the thin dense layer formed in step e (i) that has no columnar pores; and h. cross-linking the material obtained in step g.

Preferably in step a the solution is substantially free of particles

Using the method according to the invention one is able to prepare porous tissue scaffold material with a wide range of columnar pores having a narrow pore ECD standard deviation $ECD_{SD}$. This is achieved by using a temperature profile of the cooling step from $T_4$ to $T_3$ which controls the speed of the freeze-front through the biocompatible polymer solution. In general the average columnar pore diameter decreases with an increase in the rate at which the freeze front travels. This ability to tune the average columnar pore diameter is advantageous because different cell types require a different environment with respect to geometry and mechanical properties.

In one embodiment the method of the present invention prepares porous tissue scaffold material which has a uniform columnar porous structure and an average columnar pores ECD in the range of from about 10 to about 1000 microns, preferably in the range of from about 50 to about 1000 microns and more preferably in the range of from about 50 to about 500 microns and especially in the ranges of from about 100 to about 500 micron.

A second aspect of the invention provides a porous material obtainable by a method as described, and preferred, in the first aspect of the invention.

Preferably the material according to the second aspect of the invention is a porous tissue scaffold.

A third aspect of the invention provides an in-vitro cell culturing system comprising a porous tissue scaffold according to the second aspect of the invention.

A fourth aspect of the invention provides an implantable biocompatible article comprising a porous tissue scaffold material according to the second aspect of the invention.

A fifth aspect of the invention provides an implantable biocompatible article comprising the porous tissue scaffold material according to the second aspect of the invention for use as a bone filling material or bone filler, preferably a dental bone filler.

A sixth aspect of the invention provides an implantable biocompatible article comprising the porous tissue scaffold material according to the second aspect of the invention for use as a microcarrier for cells preferably pluripotent cells.

The invention will be explained in more detail in the following, non-limiting examples.

EXAMPLES

General Method

1. After dissolution of the biocompatible polymer, the sample solution was degassed at reduced pressure (preferably lower than 90 mbar for at least 5 minutes).
2. The sample was subsequently filtered through a sterilizing (0.2 micron) syringe filter and deposited in a cylindrical thermally conducting Teflon-coated thin-walled aluminium container the sides of which are thermally insulated with a Teflon bush and insulating polymer foam between the Teflon bush and the aluminium sides.
3. The sample was optionally gelled at a reduced temperature $T_0$ to $T_1$, preferably at a temperature between the sample Tm and +25° C.
4. The liquid or gelled sample solution was then directionally frozen by:
(a) rapidly lowering the temperature of the thermally conducting surface of the sample container to a low subzero temperature $T_2$(−10 to −50° C.) to form a thin layer of frozen sample, and
(b) when a thin layer of frozen sample covers the whole of the thermally conducting surface ($T_3$, $t_3$) increasing the temperature of the thermally conducting surface to the subzero temperature $T_4$ needed for the desired sample freezing rate.
(c) gradually lower the temperature experienced by the thermally conducting surface, the rate of temperature drop being dictated by the desired pore structure and pore size ($T_4$, $t_4$ to $T_5$, $t_5$). The T-profile $T_4$ to $T_5$ is not necessarily linear but can be optimised by a person skilled in the art.

The frozen samples are dried under a vacuum as is common in the art to produce dried and porous scaffolds. The scaffold is then cross-linked in the absence of water by one of the many commonly used agents (hexamethylene diisocyanate (HMDIC), EDC, glutaraldehyde, etc.) or a process (heating under a vacuum condition).

Comparative Example 1

The basic collagen suspension used in this example was prepared from commercially available calf skin collagen type I, Sigma-Aldrich, prod. nr C3511. An amount was weighed in a flask and water was added to make a 2% (mass percent) dispersion. Then HCl was added to adjust the pH value to 3.2. According to (Schoof, Apel et al. 2001) acetic acid should be added to make directional pore structures. So, 2.5 wt % acetic acid was added to the sample. This collagen preparation is a fibrillar, insoluble type I collagen which is isolated from bovine skin. According to Schoof this suspension is a polydisperse system containing low concentrations of molecules, fibrils, and fibres. The length and the width of the collagen aggregates vary in a wide range. Subsequently the dispersion was centrifuged to remove bubbles and an amount of 204 grams was deposited into a freezing container. The sample was allowed to cool to 2° C. in a refrigerator for 2 hours and then placed in a chill bath at −5° C. to allow complete freezing.

Results

The sponge structure after drying showed directional pores. The pore structure homogeneity however was not very good

Comparative Example 2

Purified recombinant CBE3 gelatin (prepared as described in Example 1 of EP 0926543 or Example 1 of EP 1014176 which example are herein incorporated by reference) was used for the sample. The ethanol (abs) was from J. T. Baker. The water used was ultrafiltrated and deionized to the same specifications as pharmaceutical grade Water For Injection (WFI). The solution was filtered by passing through a Whatman PURADISC® 25 AS (PES) syringe filter 0.2 pm, using a 10 ml NORM-JECT® luer syringe. The container used for sample freezing and drying was a 0.1 mm thick polystyrene 10 cm×10 cm×2 cm (2 cm=height) cup. The freeze dryer used was a Zirbus 3×4×5 Sublimator. An AZ 8852 dual input type K/J/T thermometer with a Thermo-Electra handheld probe nr. 80106 was used for solution temperature measurements. Optical sponge inspection was done using an Olympus SZX12 microscope equipped with an Olympus digital camera C-3040ZOOM and DP-Soft V3.2 software. Sample lighting was done using either the internal light source or a FOSTEC™ DCR (DDL) external light source. A Jeol JSM-6330F Field Emission Scanning Electron Microscope was used for generating SEM images. Sample cutting was done manually using GEM® stainless steel razor blades (uncoated).

Sample Preparation

An amount of recombinant gelatin CBE3 was weighed and transferred into a 300 ml flask and hot water (50~60° C.) was subsequently added to make a 4% (mass percent) concentration. The CBE3 solution was then stirred with a magnetic stirrer at 50° C. in a thermobath for 30 minutes to completely dissolve the gelatin. While the solution was allowed to cool to room temperature it was degassed for 15 minutes under a vacuum of 20 to 90 mbar. Care was taken that no excessive boiling occurred by manually controlling the vacuum whenever such effect was observed or anticipated. The sample solution (20.4 g) was added into the freezing container using a syringe and a 0.2 micron PES syringe filter. Care was taken to remove all surface-adhering bubbles appearing in the samples during or after filling. The CBE3 solution was then allowed to cool to 2° C. for 2 hours in a refrigerator and then put in a chill bath at −5° C.

Results

The sample remained in a gel state and did not freeze within at least 24 hours. After slightly disturbing the sample the sample immediately started freezing at the disturbed location. This shows that directional freezing from the bottom-up is impossible according this method.

Comparative Example 3

An amount of CBE3 was weighed, transferred into a 300 ml flask and hot water (50-60° C.) was added to make a 4% (mass percent) concentrated solution. The solution was then stirred with a magnetic stirrer at 50° C. in a thermobath for 30 minutes to completely dissolve the gelatin. While the solution was cooling to room temperature it was degassed for 15 minutes under a vacuum of 20 to 90 mbar. Care was taken that no excessive boiling occurred by manually controlling the vacuum whenever such effect was observed or anticipated. The solution was subsequently added in aliquots of 20.4 grams to the freezing containers using a syringe and a 0.2 micron PES syringe filter. Care was taken to remove all surface-adhering bubbles appearing in the samples during or after filling. For all samples PE-foil is used as a cover to exclude airborne dust and prevent the evaporation of water or ethanol from the top of the sample.

The sample solutions were gelled by putting them in a refrigerator at 2° C. for at least 3 hours. The (pre-gelled) sample was then subjected to freezing condition of −10° C. in the thermostatic circulator bath (2 to 3 mm deep) for 45 minutes until completely frozen. The frozen sample was then dried under a vacuum for 2 days. Cross-linking by DeHydroThermal (DHT) treatment was carried out with the samples cut to the desired size by heating them in a vacuum oven at 160° C. at a pressure less than 2 mbar for 2 days.

Results

Figure 4:
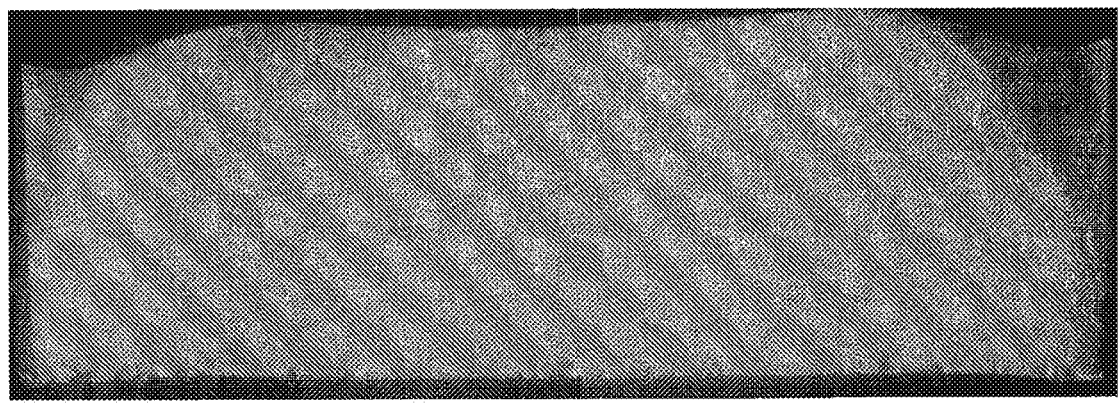
FIG. 4 shows an optical micrograph of a lateral cross-section of the entire Comparative Example 3. The sample height is 12 mm and the sample circular diameter is 4.5 cm.
Figure 5:
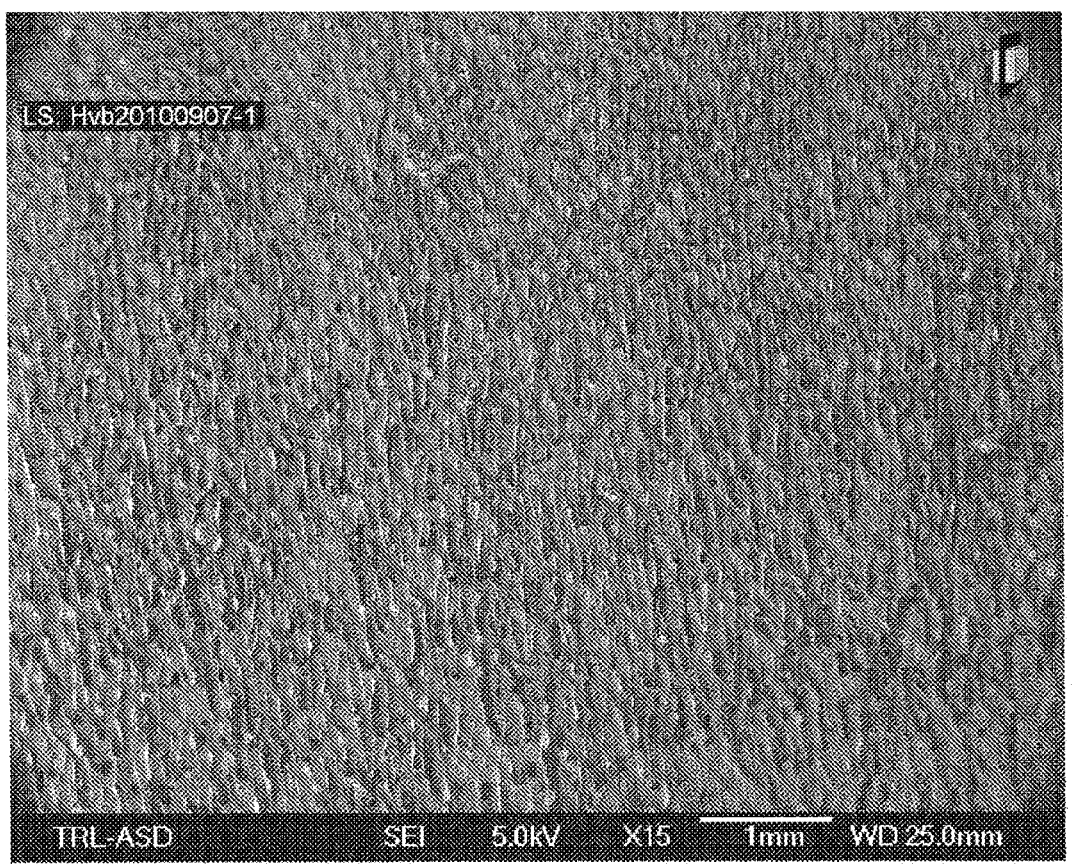
FIG. 5 shows a SEM image of a lateral (vertical) cross-section of Comparative Example 3 cut in the upper sample region
Figure 6:
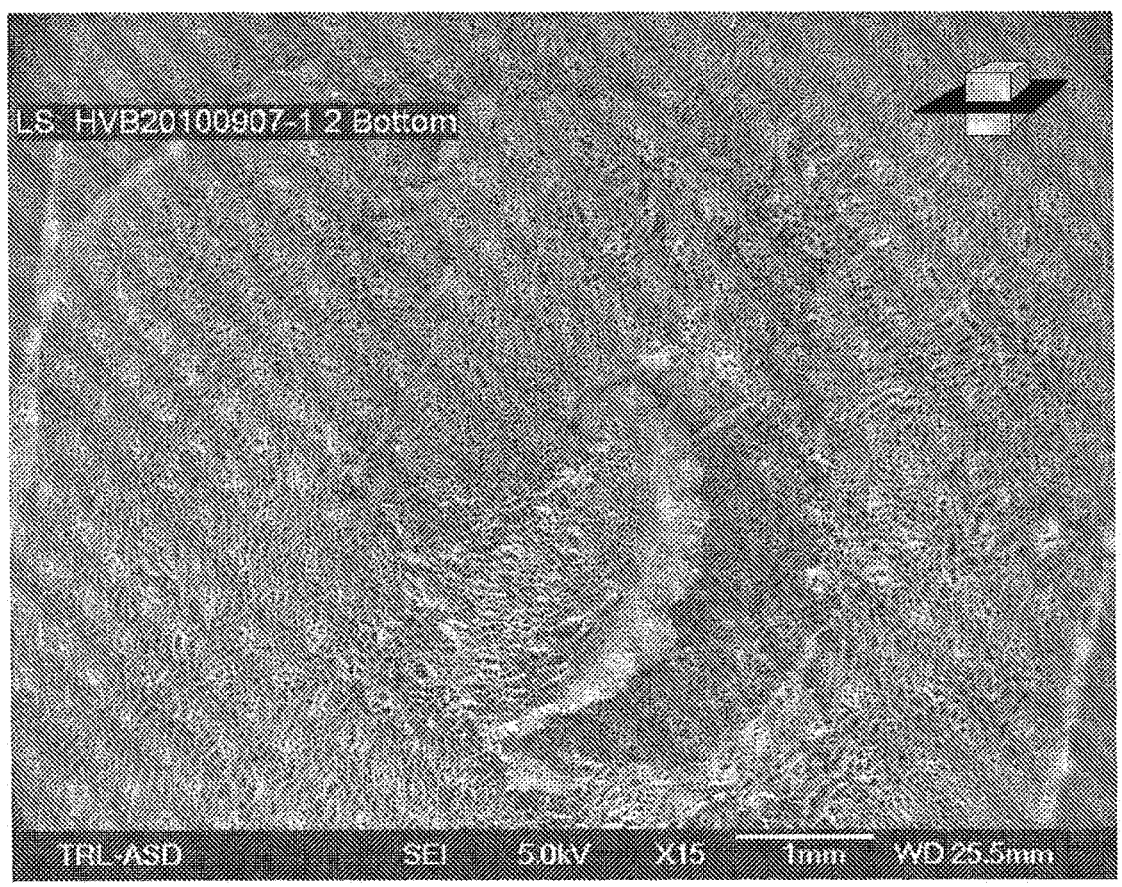
FIG. 6 shows a SEM image of a transversal (horizontal) cross-section of Comparative Example 3 cut in the bottom sample region
Figure 7:
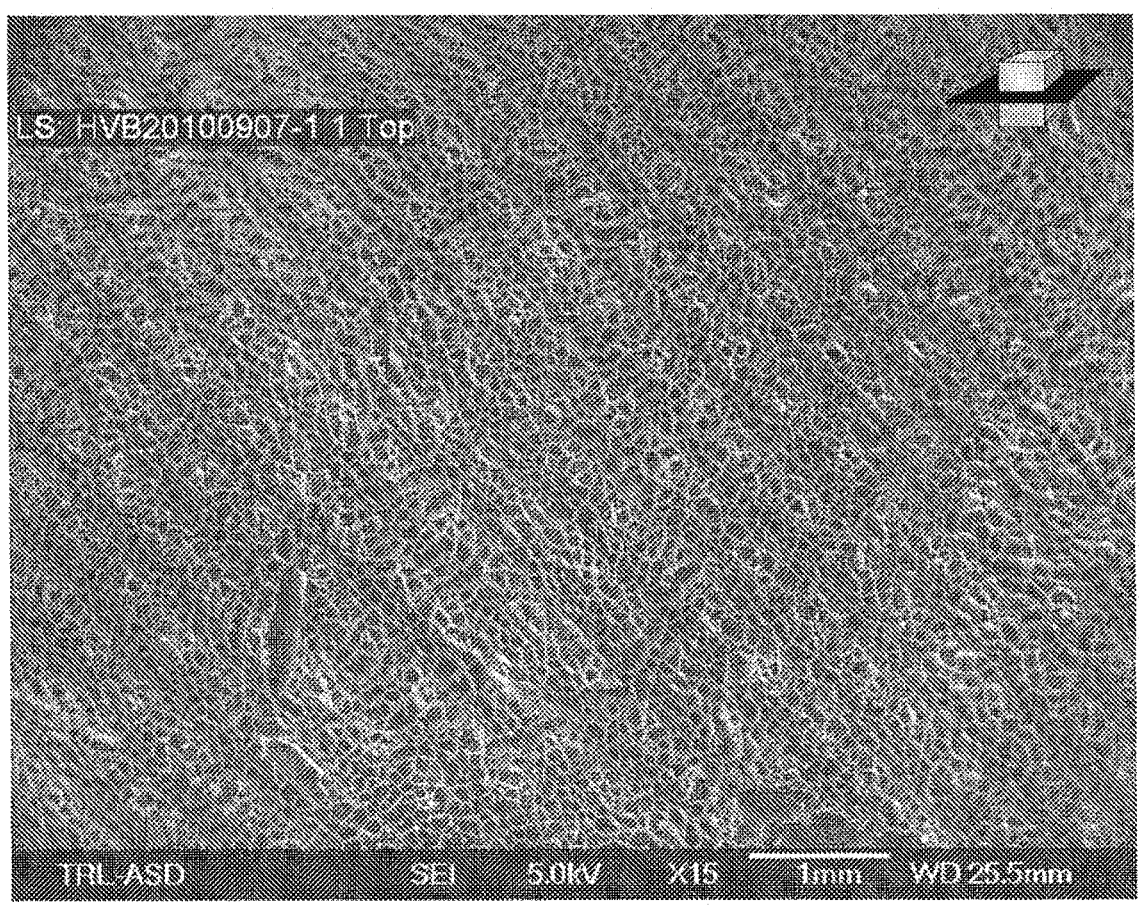
FIG. 7 shows a SEM image of a transversal (horizontal) cross-section of Comparative Example 3 cut in the top sample region

The resulting pore structure was columnar (See FIGS. 4 and 5). However, there is a large unwanted difference of pore size from bottom (50 micron) to top (100 micron), See also FIGS. 6 and 7. The roundness is better than 0.5. The average pore ECD at the top is 155 micron with an $ECD_{SD}$ of 46 micron.

Comparative Example 4

An amount of CBE3 was weighed, transferred into a 300 ml flask and hot water (50~60° C.) was added to make a 4% (mass percent) solution. The solution was then stirred with a magnetic stirrer at 50° C. in a thermobath for 30 minutes to completely dissolve the gelatin. While the solution was allowed to cool to room temperature it was degassed for 15 minutes under a vacuum of 20 to 90 mbar. Care was taken that no excessive boiling occurred by manually controlling the vacuum whenever such effect was observed or anticipated. The solution was subsequently added in aliquots of 20.4 grams to the freezing containers using a syringe and a 0.2 micron PES syringe filter. An amount of 0.2 g ethanol (abs.) was added at this point by slowly adding the solvent through a 0.2 micron PES syringe filter and the mix was stirred by creating an liquid flow using a pipette. Care was taken to remove all surface-adhering bubbles appearing in the samples during or after filling. For all samples PE-foil was used as a cover to exclude airborne dust and prevent evaporation of water or ethanol from the top of the sample. The sample solution was gelled in a refrigerator set at 2° C. for at least 3 hours. The (pre-gelled) sample was then subjected to a freezing condition of −10° C. in the thermostatic circulator bath (2 to 3 mm deep) for 45 minutes until completely frozen. The frozen sample was then dried under a vacuum for 2 days. Cross-linking by DeHydroThermal (DHT) treatment was carried out with the samples cut to the desired size by heating them in a vacuum oven at 160° C. at a pressure less than 2 mbar for 2 days.

Results

Figure 12:
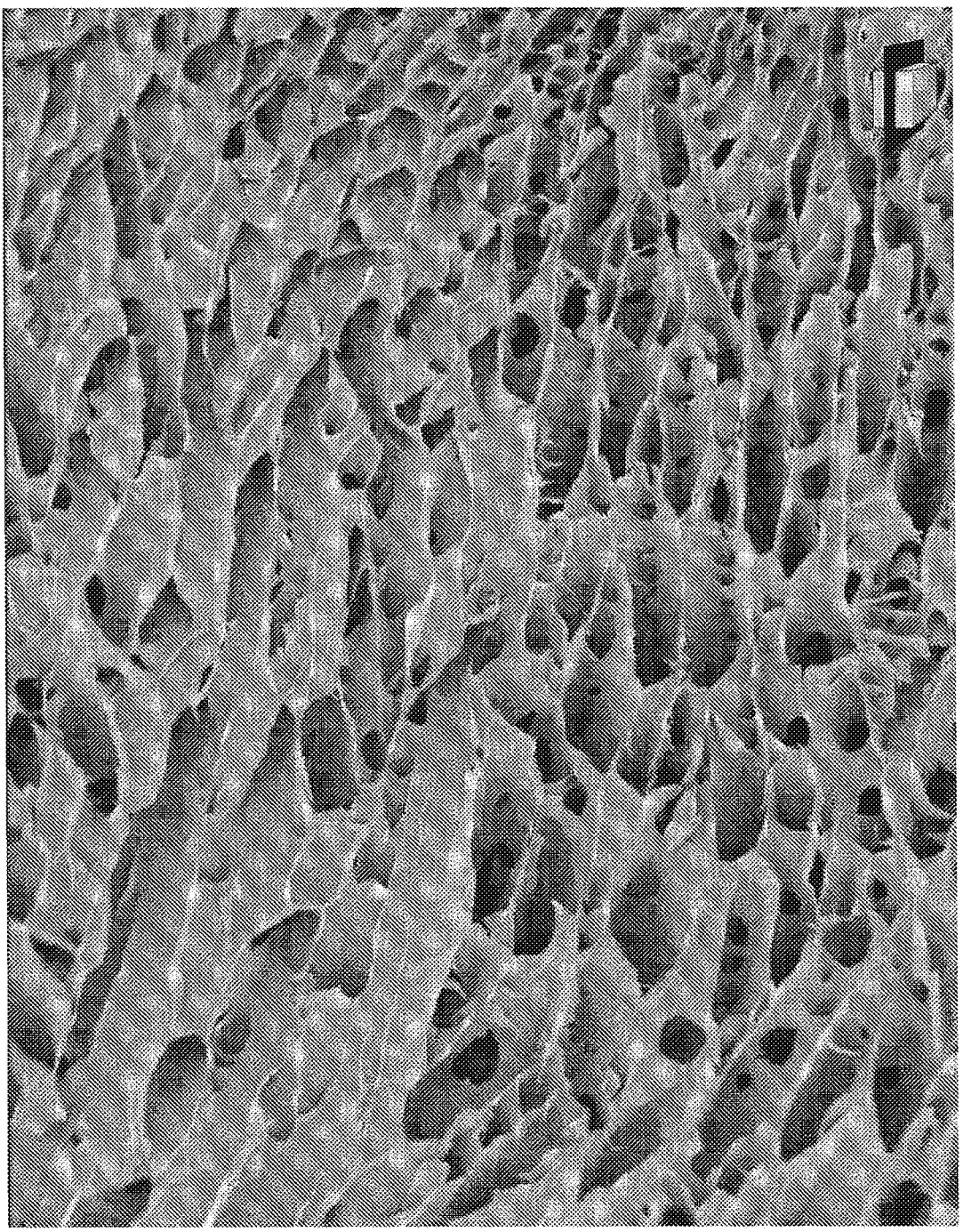
FIG. 12 shows a SEM image of a lateral (vertical) cross-section of Comparative Example 4 cut near the top of the sample.
Figure 13:
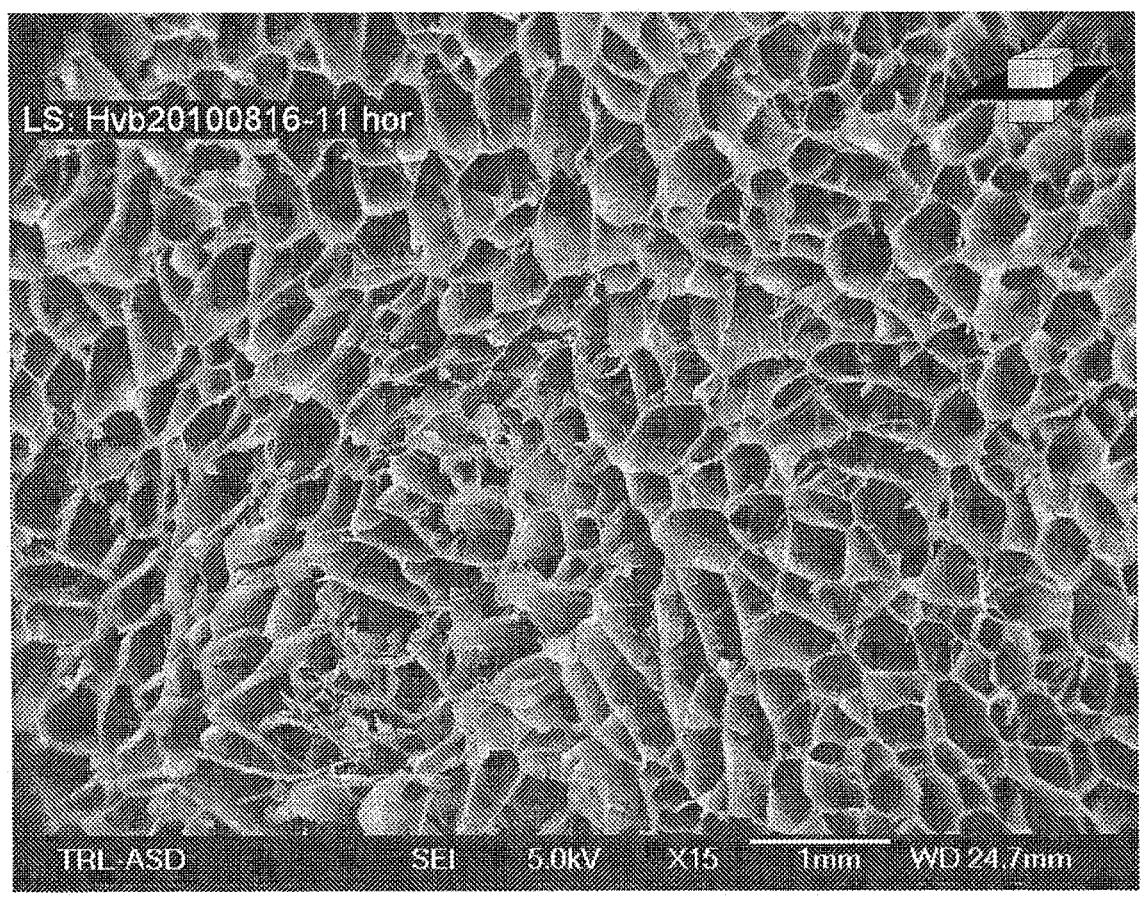
FIG. 13 shows a SEM image of a transversal (horizontal) cross-section of Comparative Example 4 cut in a region near the top of the sample.
Figure 14:
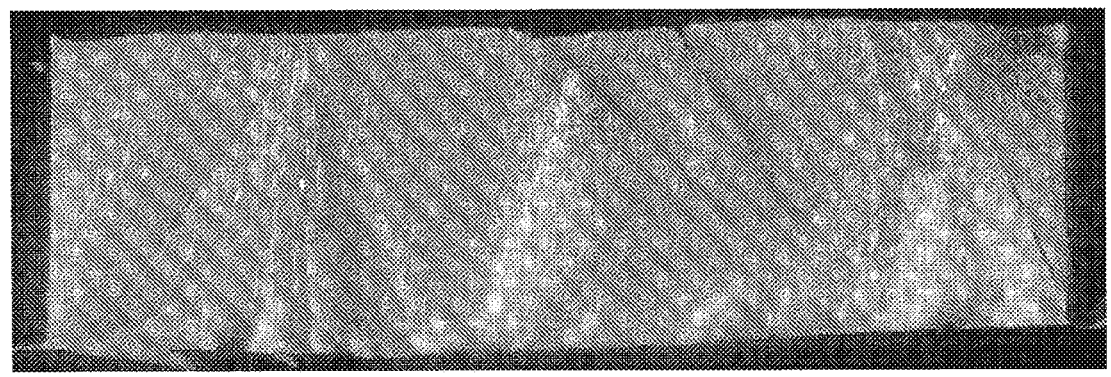
FIG. 14 shows an optical micrograph of a lateral cross-section of the Entire Comparative Example 5. The sample height is 12 mm and the sample circular diameter is 4.5 mm.
Figure 15:
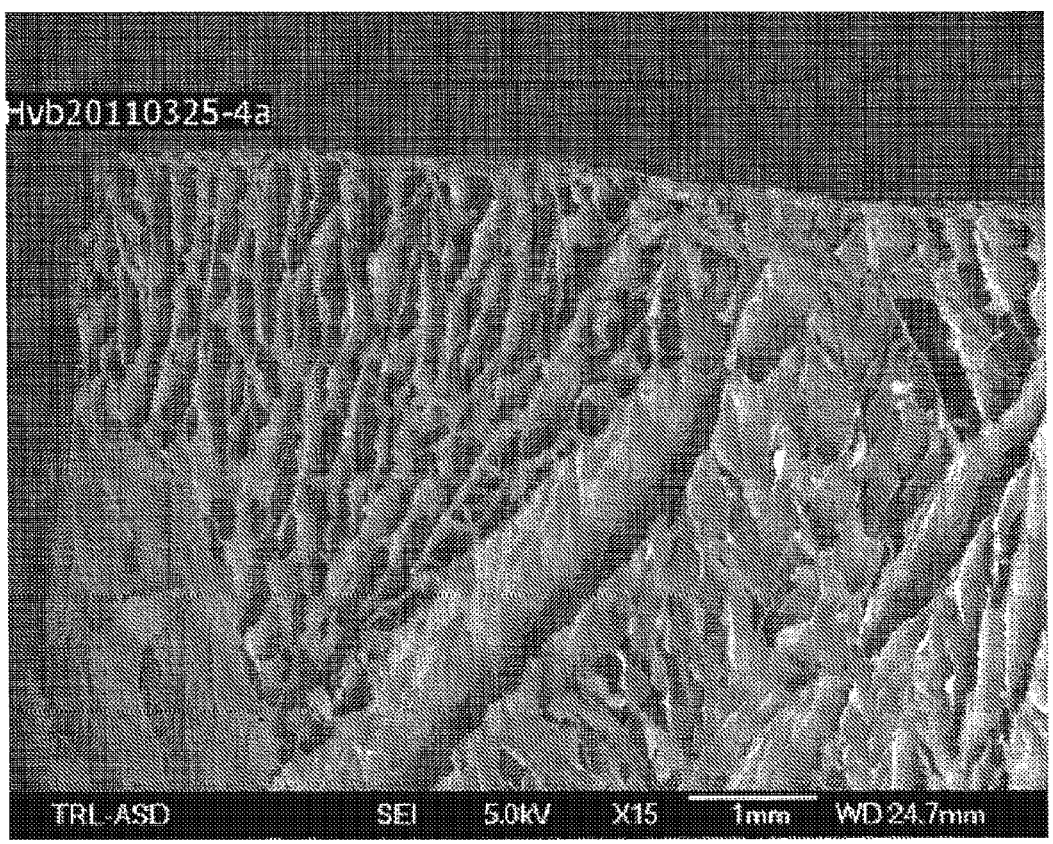
FIG. 15 shows a SEM image of a lateral (vertical) cross-section of Comparative Example 5 cut near the top of the sample

The resulting pore structure was rather homogeneous over the sample volume with columnar pores of narrow size distribution and large average size of approx. 350 micron (see FIG. 13). There was however a slight but still unwanted difference of pore size from bottom to top due to the constant temperature chill bath (see FIG. 12).

Comparative Example 5

An amount of CBE3 was weighed, transferred into a 300 ml flask and hot water (50~60° C.) was added to make an 8% (mass percent) solution. The solution was then stirred with a magnetic stirrer at 50° C. in a thermobath for 30 minutes to completely dissolve the gelatin. While the solution was allowed to cool to room temperature it was degassed for 15 minutes under a vacuum of 20 to 90 mbar. Care was taken that no excessive boiling occurred by manually controlling the vacuum whenever such effect was observed or anticipated. The solution was subsequently added in aliquots of 20.4 grams to the freezing containers using a syringe and a 0.2 micron PES syringe filter. An amount of 0.2 g ethanol (abs.) was slowly added through a 0.2 micron PES syringe filter and the mix was stirred by "jetting" using a pipette. Care was taken to remove all surface-adhering bubbles appearing in the samples during or after filling. For all samples PE-foil was used as a cover to prohibit the sedimentation of airborne dust and evaporation of water or ethanol from the top of the sample.

The sample solution was gelled in a refrigerator set at 2° C. for 45 minutes. The (pre-gelled) sample was then subjected to a freezing condition of −10° C. in a chill bath (2 to 3 mm deep) for 45 minutes until completely frozen. The frozen sample was then dried under a vacuum for 2 days. Cross-linking by DeHydroThermal (DHT) treatment was carried out with the samples cut to the desired size in a vacuum oven at 160° C. and a pressure less than 2 mbar for 2 days.

Result

Figure 16:
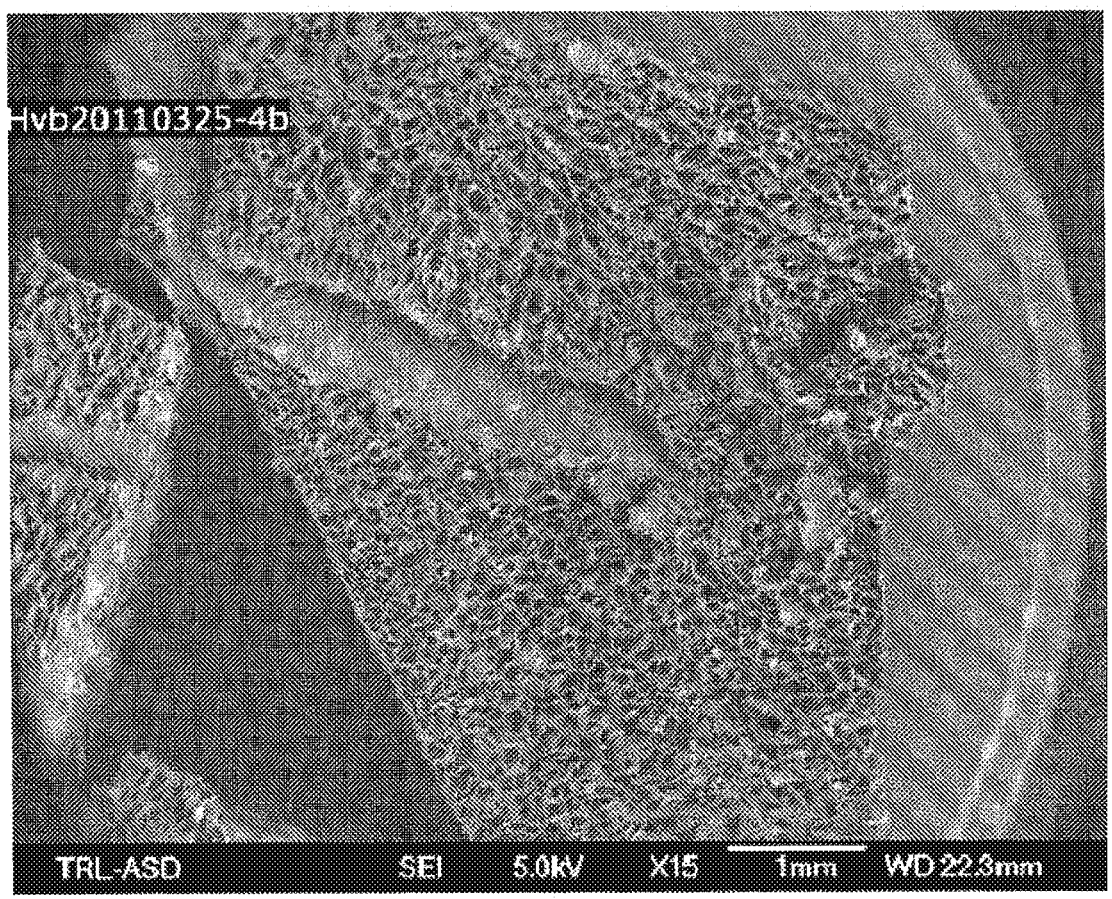
FIG. 16 shows a SEM image of a transversal (horizontal) cross-section of Comparative Example 5 cut near the bottom region of the sample just above the nucleation layer
Figure 17:
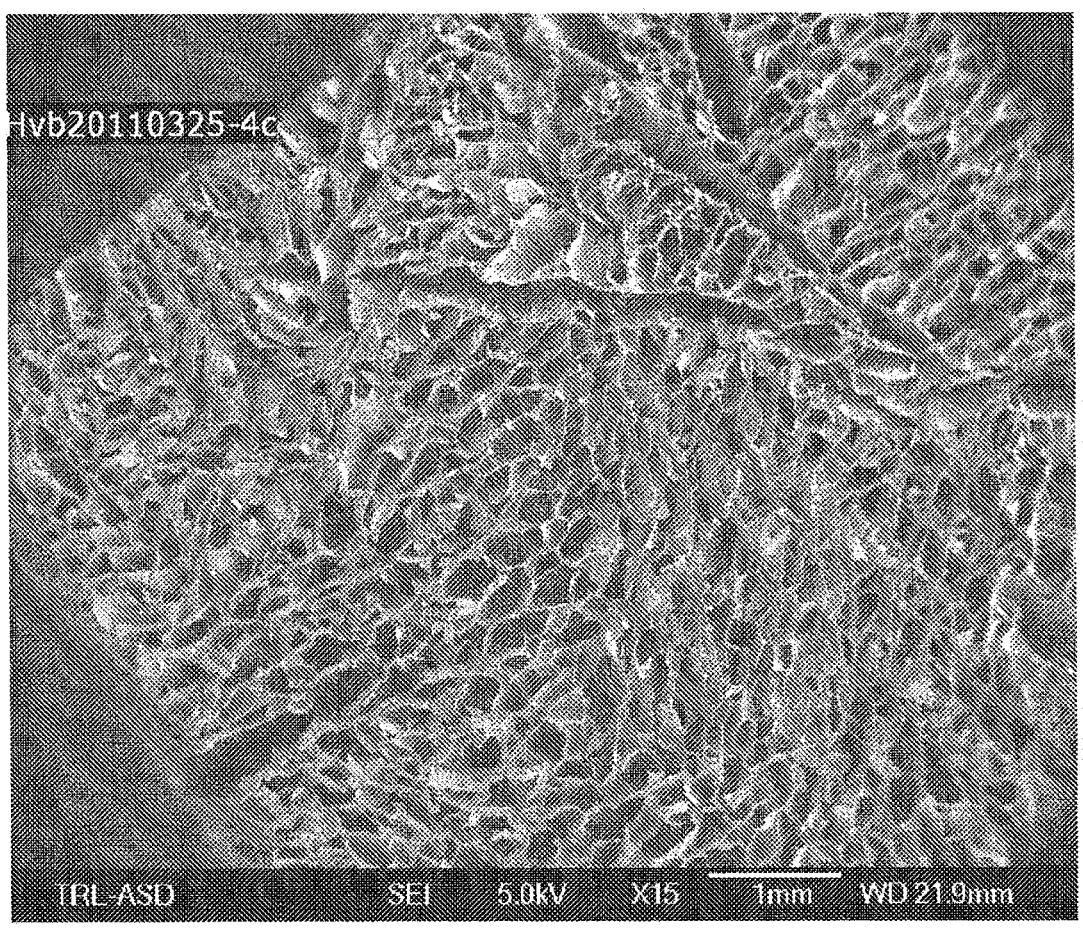
FIG. 17 shows a SEM image of a transversal (horizontal) cross-section of Comparative Example 5 cut near the top of the sample.

The resulting pore structure was columnar over the sample volume with columnar pores of narrow size distribution and large average size of approx. 350 micron in the upper sample half. Columnar pore widening from the lower to the upper sample volume was also seen, see FIGS. 16 and 17. It is believed that this was due to the use of a constant chill bath temperature instead of a gradual temperature ramp. Thus, as the freezing front moves away from the cooled container, the local freezing temperature was expected to be ever higher and due to this the pores were growing larger.

Comparative Example 6

An amount of CBE3 was weighed, transferred into a 300 ml flask and hot water (50–60° C.) was added to make a 7.5% (mass percent) solution. The solution was then stirred with a magnetic stirrer at 50° C. in a thermobath for 30 minutes to completely dissolve the gelatin. While the solution was allowed to cool to room temperature it was degassed for 15 minutes under a vacuum of 20 to 90 mbar. Care was taken that no excessive boiling occurred by manually controlling the vacuum whenever such effect was observed or anticipated. The solution was then added in aliquots of 20.4 grams to the freezing containers using a syringe and a 0.2 micron PES syringe filter. Care was taken to remove all surface-adhering bubbles appearing in the samples during or after filling. For all samples PE-foil was used as a cover to exclude airborne dust and prevent the evaporation of water or ethanol from the top of the sample. The sample solution was gelled by placing in a refrigerator at 2° C. for 1 day. The sample was then placed in a chill bath set at 18° C. and pump A was started, pumping very cold (−72±2° C.) liquid (ethanol) into the chill bath with vigorous mixing at such a rate that the chill bath temperature dropped at a rate of 22° C./min until the chill bath temperature reached −52° C. During this T-ramping the first appearance of ice formation was observed at a chill bath temperature of −16° C. Within 10 minutes the sample volume was completely frozen. The frozen sample was then dried under a vacuum for 4 days. Cross-linking by DeHydroThermal (DHT) treatment was carried out with the samples cut to the desired size and then placed in a vacuum oven at 160° C. and a pressure less than 2 mbar for 2 days.

Result

Figure 18:
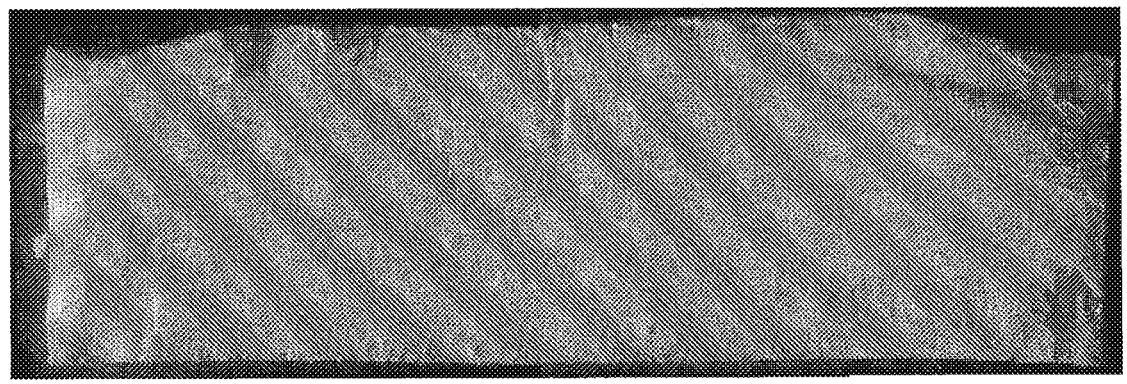
FIG. 18 shows an optical micrograph of a lateral cross-section of the entire Comparative Example 6. The sample height is 12 mm and the sample circular diameter is 4.5 mm.
Figure 19:
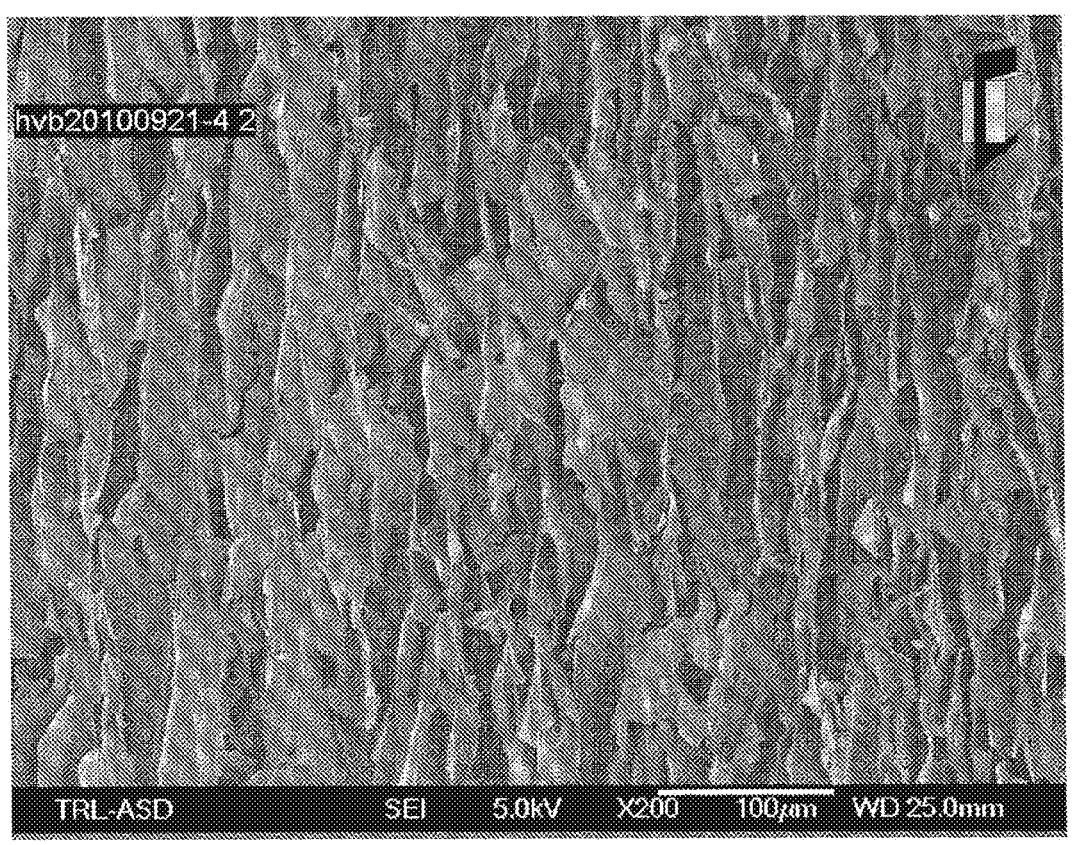
FIG. 19 shows a SEM image of a lateral (vertical) cross-section of Comparative Example 6 cut near the top of the sample.
Figure 20:
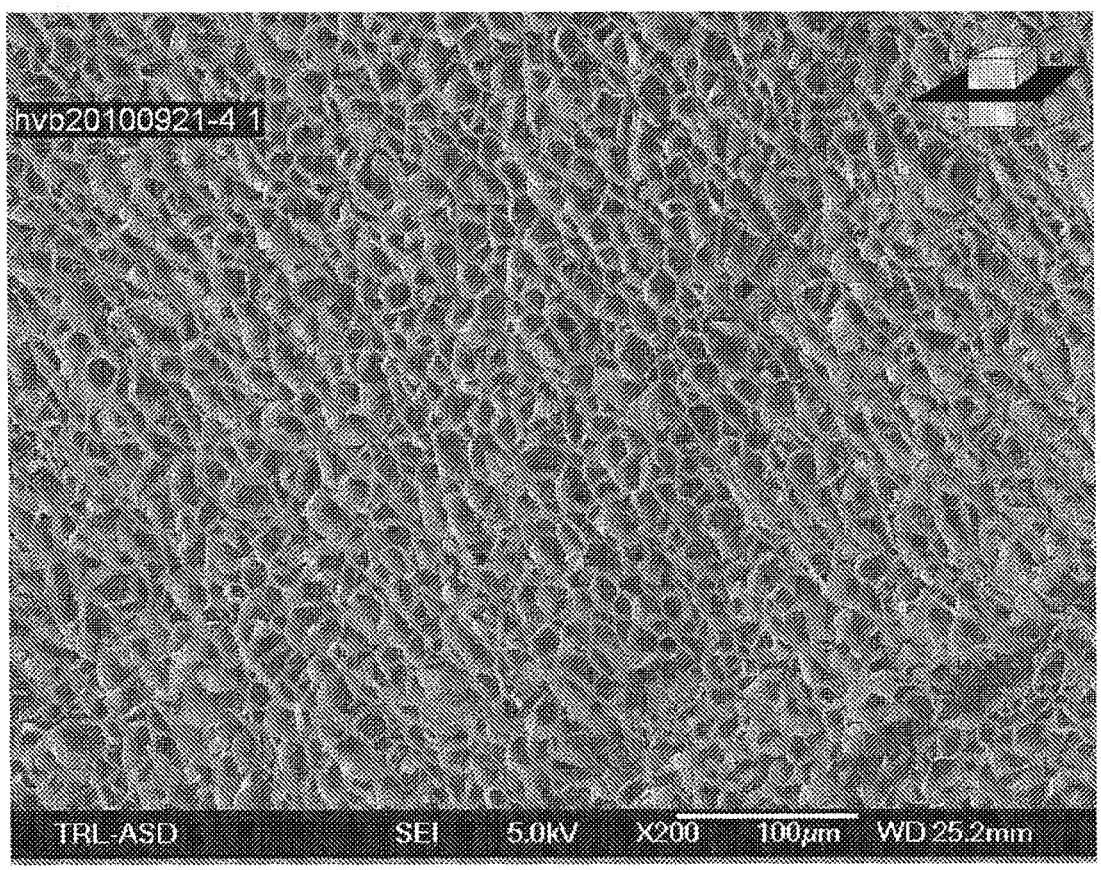
FIG. 20 shows a SEM image of a transversal (horizontal) cross-section of Comparative Example 6 cut near the bottom region of the sample just above the nucleation layer.

The resulting pore structure was columnar over the whole sample volume with columnar pores of narrow size distribution (see FIGS. 18 and 19) and very small average size of approx. 20 micron in the lower sample region (see FIG. 20). There is however still an unwanted difference of pore size from top to bottom (compare FIGS. 20 and 21).

Inventive Example 1

An amount of CBE3 was weighed, transferred into a 300 ml flask and hot water (50–60° C.) was added to make a 7.5% (mass percent) solution. The solution was then stirred with a magnetic stirrer at 50° C. in a thermobath for 30 minutes to completely dissolve the gelatin. While the solution was allowed to cool to room temperature it was degassed for 15 minutes under a vacuum of 20 to 90 mbar. Care was taken that no excessive boiling occurred by manually controlling the vacuum whenever such effect was observed or anticipated. The solution was subsequently added in aliquots of 20.4 grams to the freezing containers using a syringe and a 0.2 micron PES syringe filter. An amount of 0.2 g ethanol (abs.) was added at this point by slowly adding the solvent through a 0.2 micron PES syringe filter and the mix was stirred by "jetting" using a pipette. Care was taken to remove all surface-adhering bubbles appearing in the samples during or after filling. For all samples PE-foil was used as a cover to exclude airborne dust and prevent evaporation of water or ethanol from the top of the sample.

The sample solution was gelled in the chill bath at 10° C. for 20 minutes. The chill bath was then rapidly cooled by pumping very cold (−72±2° C.) liquid (ethanol) into the chill bath with vigorous mixing at such a rate that the chill bath temperature dropped at a rate of 28° C./min until the temperature reached −30° C. During this T-ramping the first appearance of ice formation was observed at a chill bath temperature of −25° C. Subsequently the cold liquid pump A was stopped and the chill bath temperature remained fairly constant within the time it took for the full contacting sample container to become covered with a frozen sample layer. Immediately upon full coverage the warm (+40° C.) liquid (ethanol) pump B was started at such a rate that the chill bath temperature was increased to −4° C. at a rate of approx. 100° C./minute. As soon as the chill bath temperature reached −4° C. pump B was stopped and pump A was started at a very slow rate such that the chill bath temperature was lowered at a rate of 0.1° C./min until the complete sample volume was frozen.

The frozen sample was then dried under a vacuum for 2 days. DeHydroThermal (DHT) cross-linking was carried out with the samples cut to the desired size by heating in a vacuum oven at 160° C. at a pressure less than 2 mbar for 2 days.

Results

Figure 8:
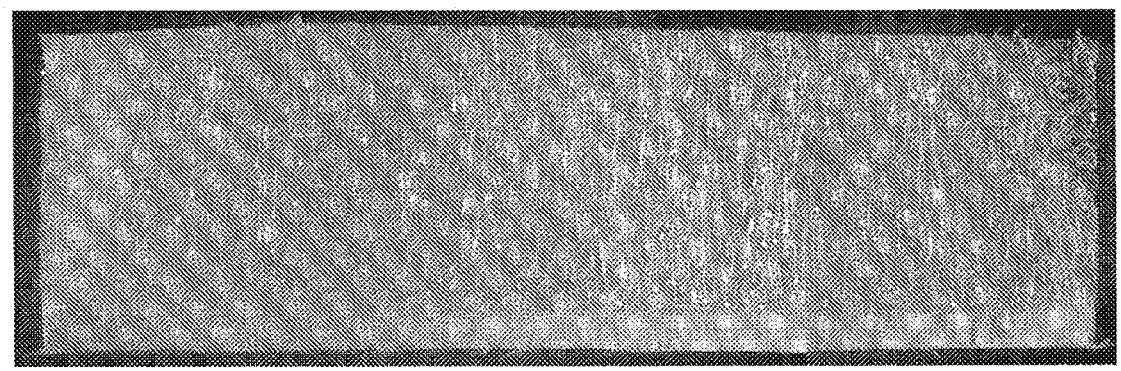
FIG. 8 shows an optical optical micrograph of a lateral cross-section of Inventive Example 1. Sample height is 12 mm sample circular diameter is 4.5 mm
Figure 9:
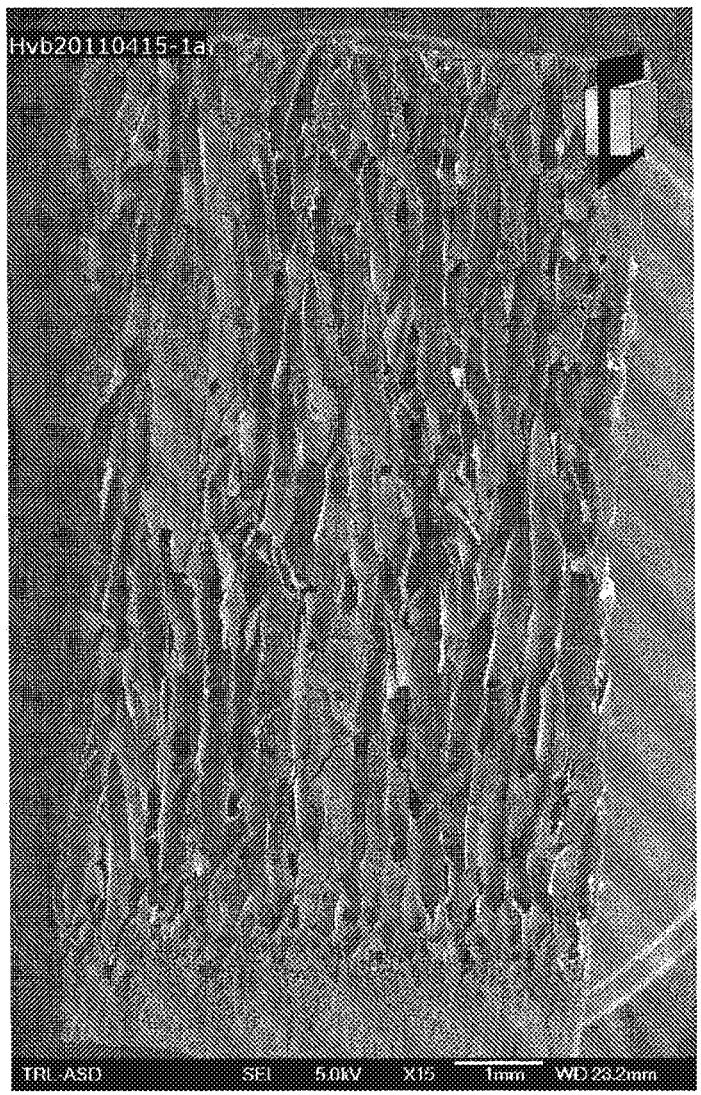
FIG. 9 shows a SEM image of a lateral (vertical) cross-section of the full sample height of a sample prepared according to Inventive Example 1 showing a thin dense nucleation layer at the bottom and uniform parallel pores from this layer to the top of the sample.
Figure 10:
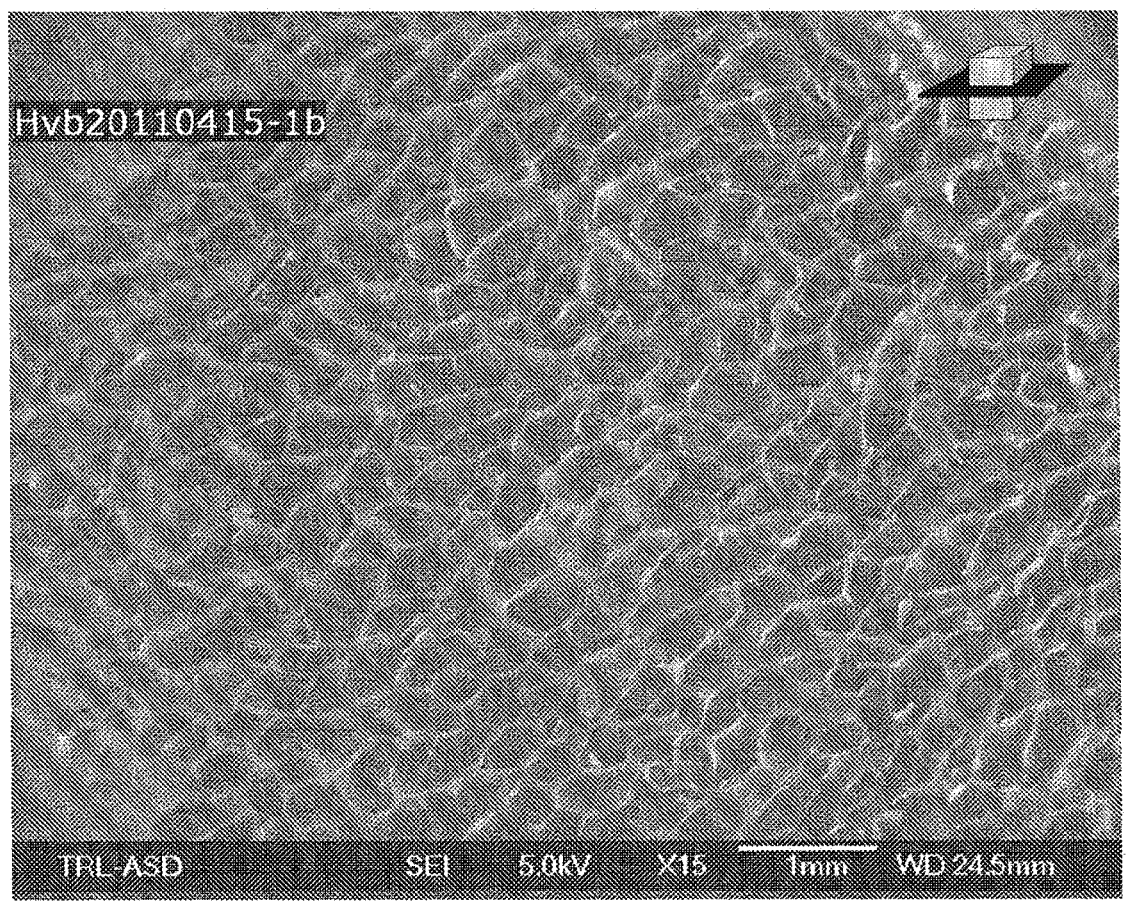
FIG. 10 shows a SEM transversal (horizontal) cross-section of Inventive Example 1 cut in the lower region, just above the nucleation layer.
Figure 11:
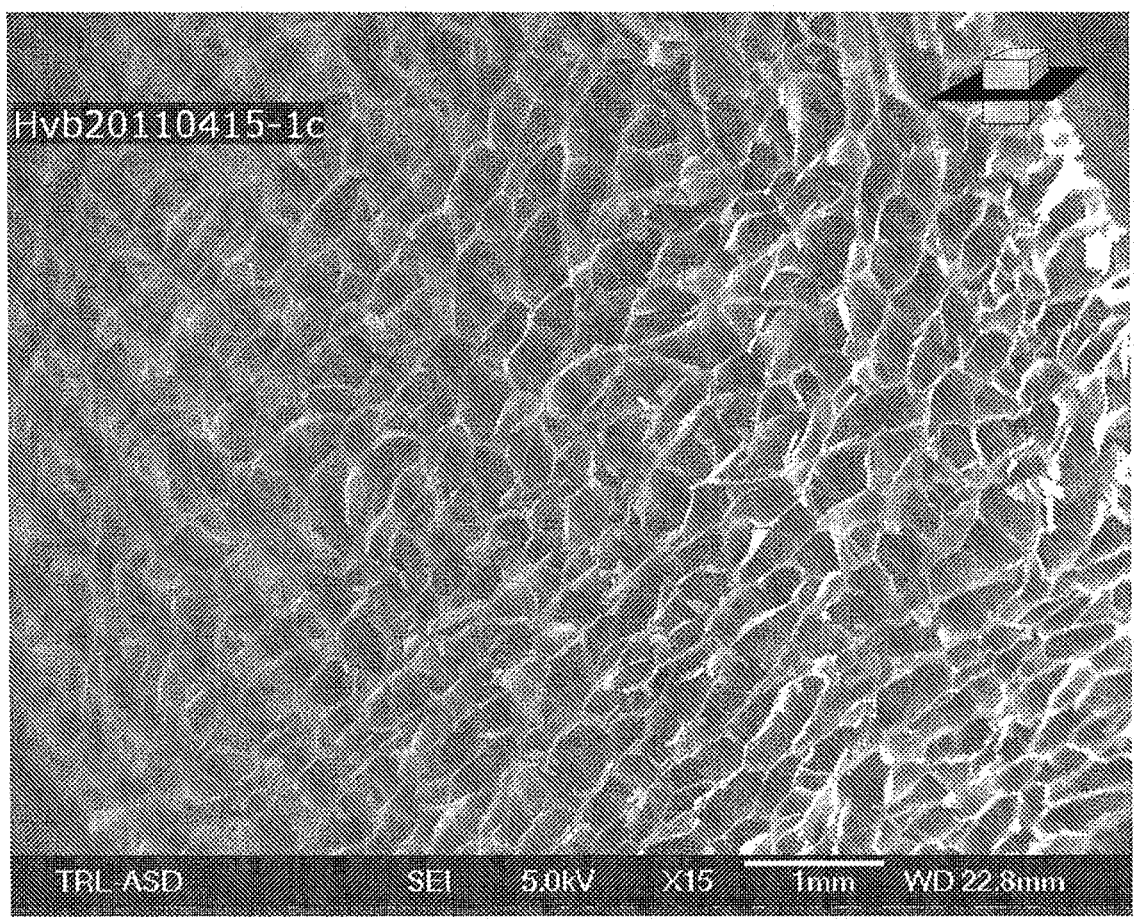
FIG. 11 shows a SEM image of a transversal (horizontal) cross-section of Inventive Example 1 cut in the top region of the sample.
Figure 21:
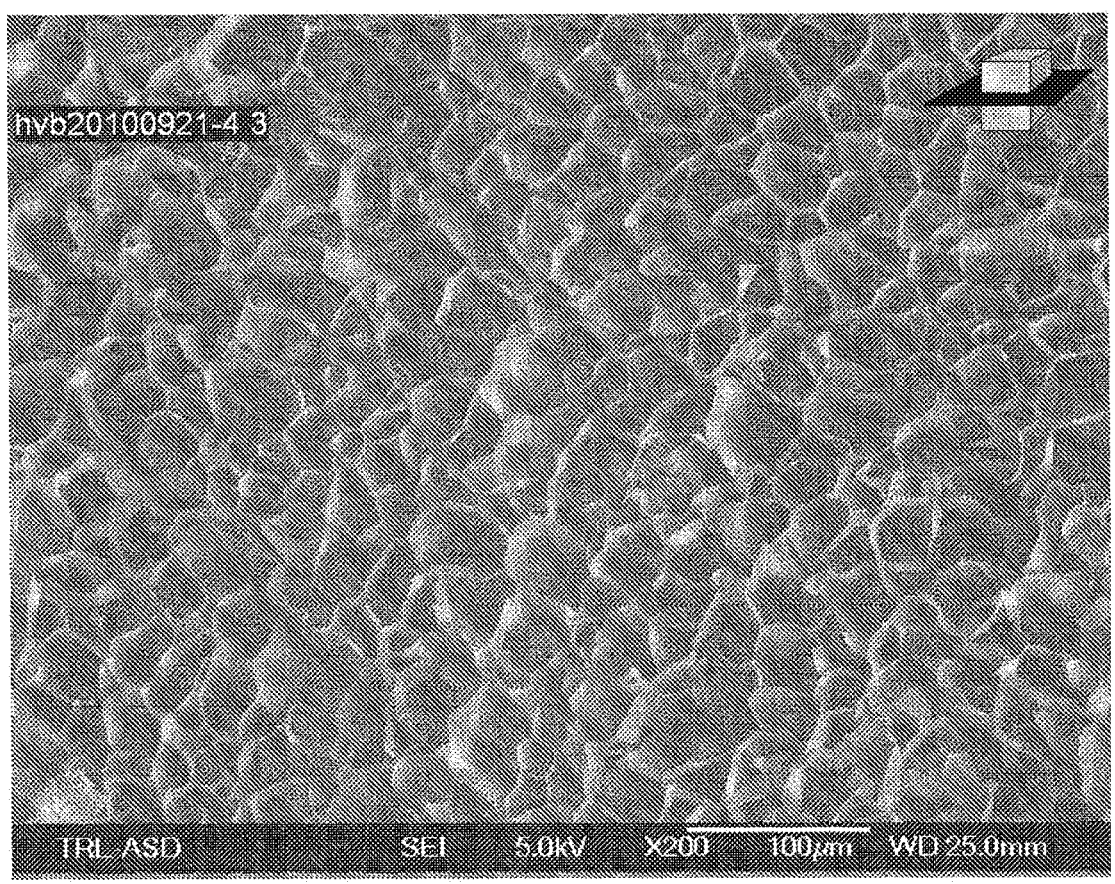
FIG. 21 shows a SEM image of a transversal (horizontal) cross-section of Comparative Example 6 cut near the top of the sample.

The resulting pore structure was very homogeneous over the sample volume with columnar pores of narrow size distribution and large average size of approx. 350 micron. The pore structure in the lower sample region was very similar to the structure in the upper sample region (FIGS. 10 and 11) in contrast to Comparative Example 6 (FIGS. 20 and 21). The roundness of the pores was higher than 0.5, as preferred. The dense nucleated bottom layer (See FIGS. 8 and 9) can be cut and discarded at will. The average pore ECD for this example was 300 micron with an $ECD_{SD}$ of 90 micron.

Inventive Example 2

An amount of deionized bone-lime gelatin was weighed, transferred into a 300 ml flask and hot water (50–60° C.) was subsequently added to make a 7.5% (mass percent) solution. The solution was stirred with a magnetic stirrer at 50° C. in a thermobath for 30 minutes to completely dissolve the gelatin. While the solution was cooling to room temperature it was degassed for 15 minutes under a vacuum of 20 to 90 mbar. Care was taken that no excessive boiling occurred by manually controlling the vacuum whenever such effect was observed or anticipated. The solution was subsequently added in aliquots of 20.4 grams to the freezing containers using a syringe and a 0.2 micron PES syringe filter. An amount of 0.2 g ethanol (abs.) was slowly adding through a 0.2 micron PES syringe filter and the mix was stirred by "jetting" using a pipette. Care was taken to remove all surface-adhering bubbles appearing in the samples during or after filling. For all samples PE-foil was used as a cover to prevent contamination by airborne dust and the evaporation of water or ethanol from the top of the sample. The sample solution was gelled in the chill bath at 10° C. for 20 minutes. The chill bath was then rapidly cooled by pumping very cold (−72±2° C.) liquid (ethanol) into the chill bath with vigorous mixing at such a rate that the chill bath temperature dropped at a rate of 28° C./minute until the chill bath temperature reaches −30° C. During this T-ramping the first appearance of ice formation was observed at a chill bath temperature of −25° C. Subsequently the cold liquid pump A was stopped and the chill bath temperature remained fairly constant within the time it took for the full contacting sample container to become covered with a frozen sample layer. Immediately upon full coverage the warm (+40° C.) liquid (ethanol) pump B was started at such a rate that the chill bath temperature was increased to −4° C. at a rate of approx. 100° C./minute. As soon as the chill bath temperature reached the desired −4° C. pump B was stopped and pump A was started at a very slow rate such that the chill bath temperature was lowered at a rate of 0.1° C./minute until the complete sample volume was frozen.

Results

The resulting pore structure was similar to Inventive Example 1. It was very homogeneous over the sample volume with columnar pores of narrow size distribution and large average size of approx. 350 micron. The pore structure in the lower sample region was very similar to the structure in the upper sample. The roundness of the pores was better than 0.5, as preferred. The dense nucleated bottom layer can be cut and discarded at will.

Inventive Example 3

An amount of kappa-carrageenan was weighed, transferred into a 300 ml flask and hot water (ca 70° C.) was added to make a 4.0% (mass percent) solution. The solution was stirred with a magnetic stirrer at 70° C. in a thermobath for 1 hour to completely dissolve the biocompatible polymer. While the solution was kept warm it was degassed for 15 minutes under a vacuum of 20 to 90 mbar. The solution was subsequently added in aliquots of 20.4 grams to the freezing containers using a syringe. Care was taken to remove any air bubbles from the solution once it was deposited in the freezing containers. For all samples PE-foil was used as a cover to prevent contamination by airborne dust and the evaporation of water or ethanol from the top of the sample. The sample solution was gelled in a refrigerator at 2° C. for 2 hours and the sample was subsequently mounted in the chill bath to a depth of a few millimeters. The chill bath was then rapidly lowered in temperature by pumping very cold (−73±3° C.) liquid (ethanol) into the chill bath with vigorous mixing at such a rate that the chill bath temperature dropped at a rate of in-between 20 to 100° C./minute until the chill bath temperature reached −30 to −40° C. During this T-ramping the first appearance of ice formation was observed at a chill bath temperature of −20 to −30° C. Immediately after the bottom of the sample contains a thin ice layer, covering the full freezing container bottom, the warm (+50° C.) liquid (ethanol) pump B was started at a high rate so that the chill bath temperature was increased at a rate of approx. 100° C./minute. As soon as the chill bath temperature reached the desired −4° C. pump B was stopped and pump A was started at a very slow rate such that the chill bath temperature was lowered at a rate of ca 0.5° C./minute until the complete sample volume was frozen.

Results

Figure 22:
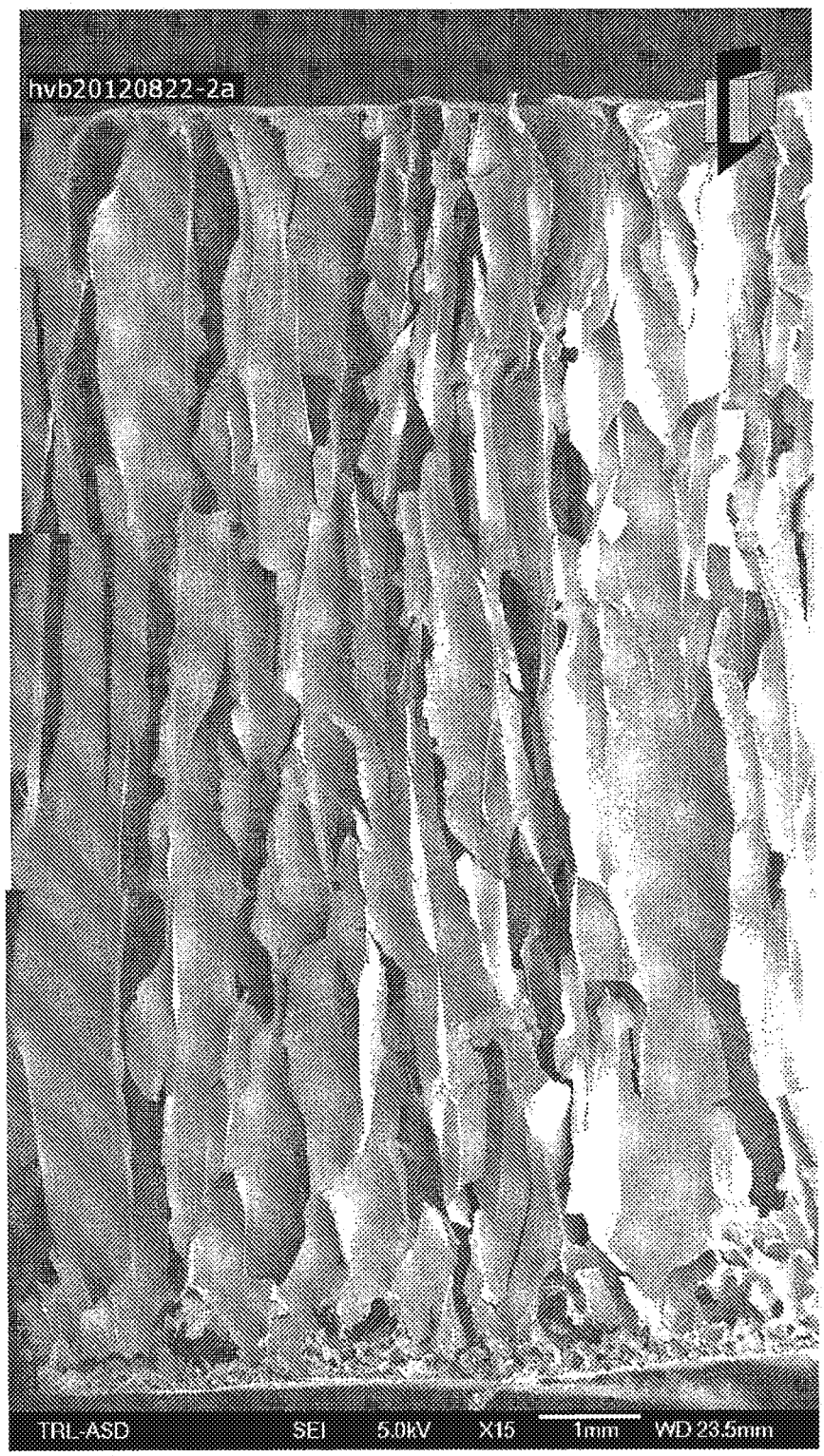
FIG. 22 shows a SEM image of a lateral (vertical) cross-section of Inventive Example 3
Figure 23:
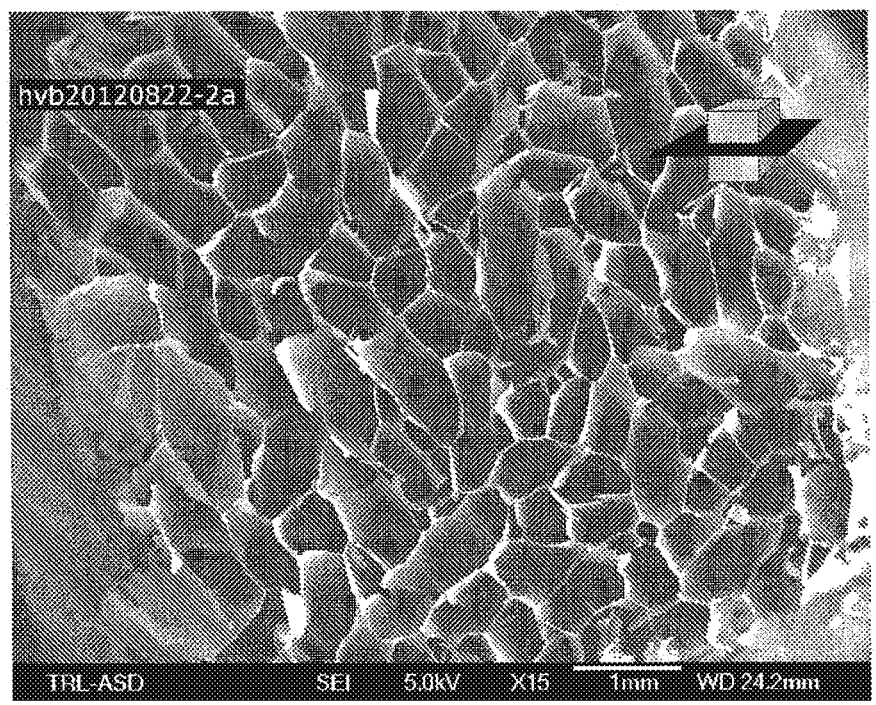
FIG. 23 shows a SEM image of a transversal (horizontal) cross-section of Inventive Example 3 cut near the bottom region of the sample just above the nucleation layer.
Figure 24:
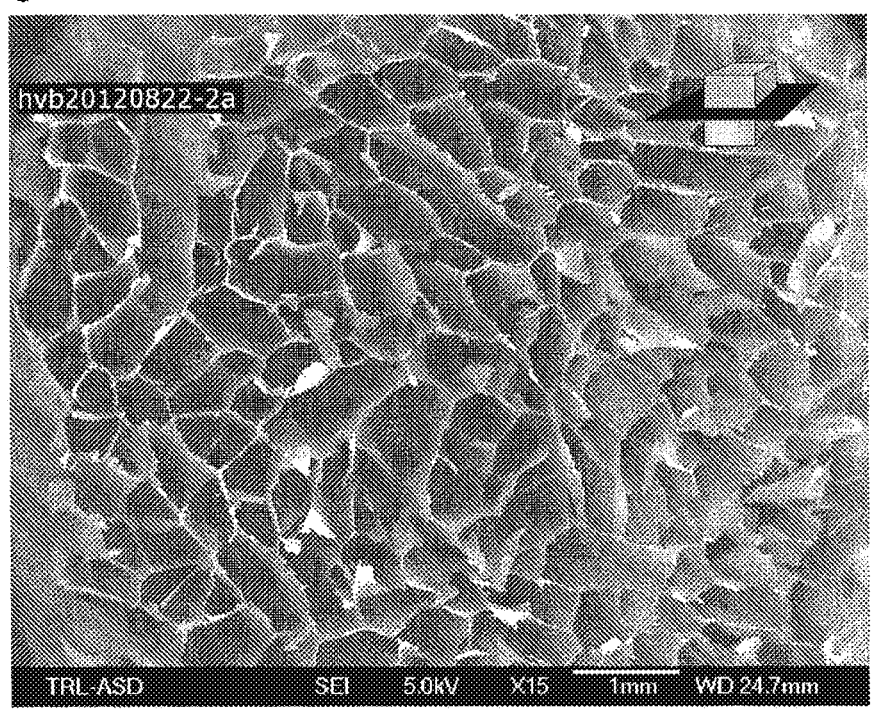
FIG. 24 shows a SEM image of a transversal (horizontal) cross-section of Inventive Example 3 cut near the top of the sample.

The resulting pore structure was similar to Inventive Example no. 1. It was very homogeneous over the sample volume with pores of narrow size distribution and a large average size of 500 to 800 micron. The pore structure in the lower sample region was very similar to the structure in the upper sample. The roundness of the pores is better than 0.5, as preferred. The average pore ECD for this example is 450 micron with an $ECD_{SD}$ of 200 micron. The dense nucleated bottom layer thickness was less than half a millimeter and can be cut and discarded at will. See FIGS. 22, 23 and 24.

Inventive Example 4

An amount of chitosan from shrimp shells was weighed, transferred into a 300 ml flask and hot water (ca 50° C.) was added to make a 7.5% (mass percent) solution. The solution was stirred with a magnetic stirrer at 50° C. in a thermobath for 1 hour to completely dissolve the biocompatible polymer. While the solution was kept warm it was degassed for 15 minutes under a vacuum of 20 to 90 mbar. The solution was subsequently added in aliquots of 20.4 grams to the freezing container using a syringe. Care was taken to remove any air bubbles from the solution once it was deposited in the freezing containers. For all samples PE-foil was used as a cover to prevent contamination by airborne dust and the evaporation of water or ethanol from the top of the sample. The sample solution was gelled in a refrigerator at 2° C. for 2 hours and the sample was subsequently mounted in the chill bath to a depth of a few millimeters. The chill bath was then rapidly lowered in temperature by pumping very cold (−73±3° C.) liquid (ethanol) into the chill bath with vigorous mixing at such a rate that the chill bath temperature dropped at a rate of in-between 20 to 100° C./minute until the chill bath temperature reached −30 to −40° C. During this T-ramping the first appearance of ice formation was observed at a chill bath temperature of −20 to −30° C. As soon as a thin ice layer covered the full freezing surface of the container, warm (+50° C.) liquid (ethanol) pump B was started at a high rate so that the chill bath temperature was increased at a rate of approx. 100° C./minute. When the chill bath temperature reached the desired temperature (−4° C.) pump B was stopped and pump A was started at a very slow rate such that the chill bath temperature was lowered at a rate of ca 0.1° C./minute until the complete sample volume is frozen.

Results

Figure 25:
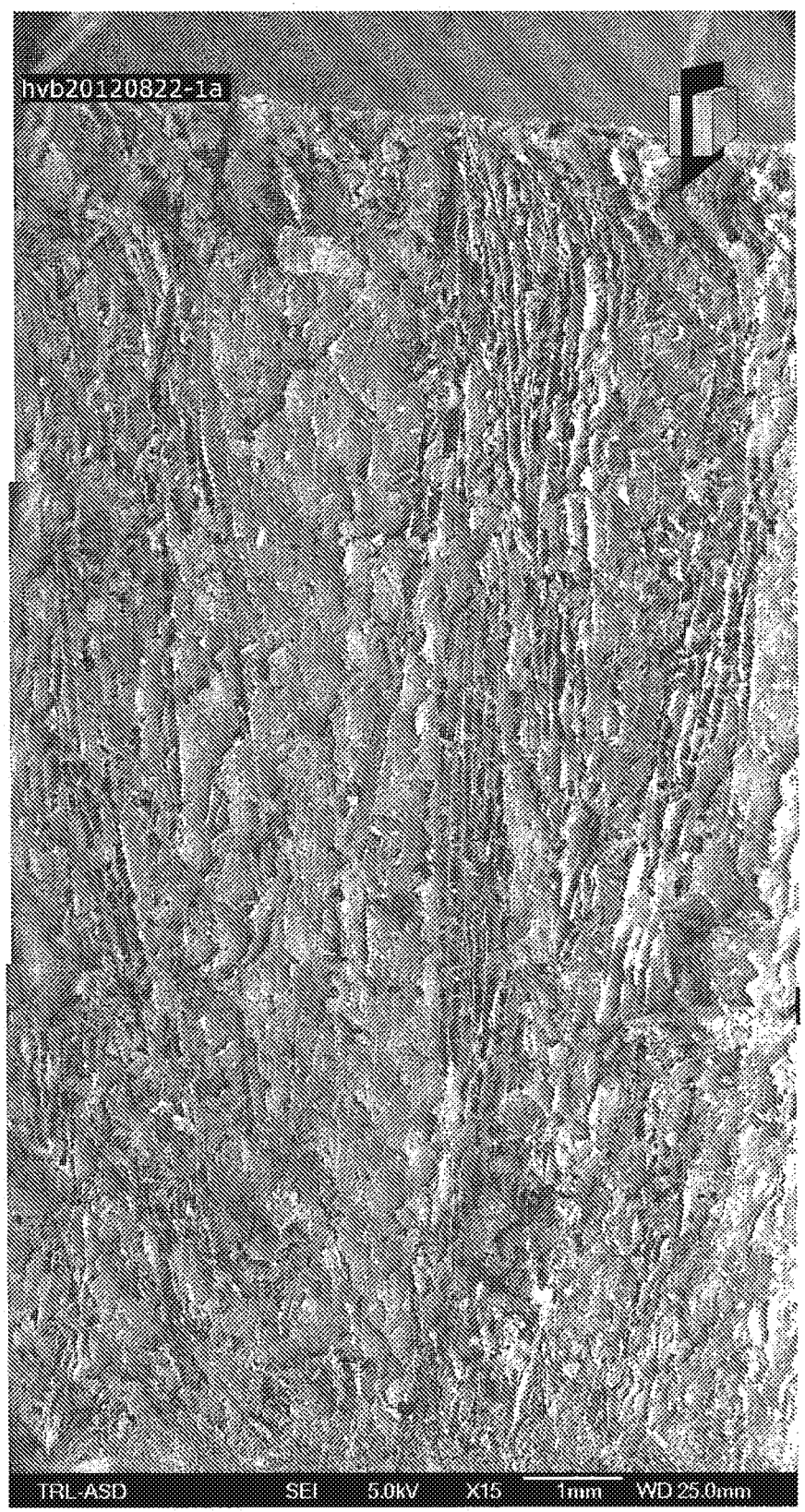
FIG. 25 shows a SEM image of a lateral (vertical) cross-section of Inventive Example 4.
Figure 26:
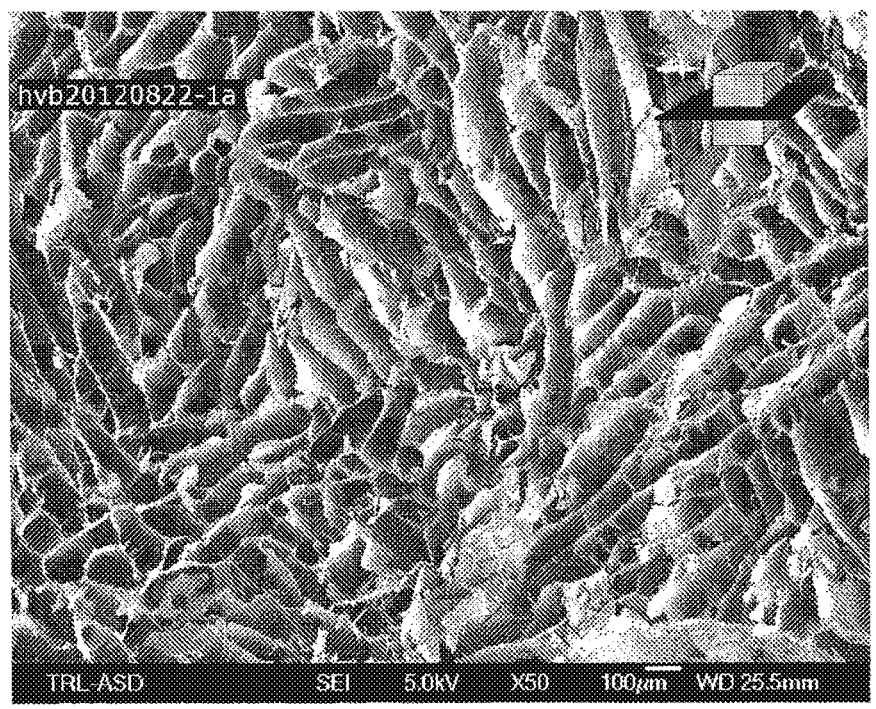
FIG. 26 Shows a SEM image of a transversal (horizontal) cross-section of Inventive Example 4 cut near the bottom region of the sample just above the nucleation layer.
Figure 27:
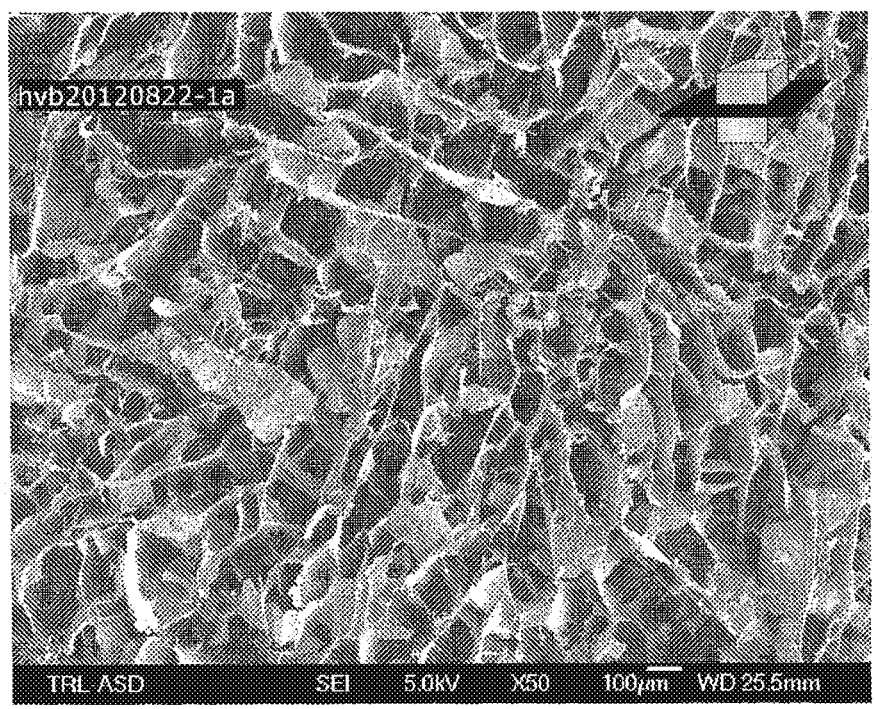
FIG. 27 shows a SEM image of a transversal (horizontal) cross-section of Inventive Example 4 cut near the top of the sample.

The resulting pore structure was very homogeneous over the sample volume with stretched pore shapes and a narrow size distribution. The average pore size was about 100 micron. The pore structure in the lower sample region was very similar to the structure in the upper sample. The average pore ECD for this example was 60 micron with an $ECD_{SD}$ of 27 micron. The dense nucleated bottom layer thickness was approx. half a millimeter and can be cut and discarded at will. See FIGS. 25, 26 and 27.

The invention claimed is:

1. A method for producing a porous material from a liquid solution comprising a biocompatible polymer selected from the group consisting of:
collagen, gelatin, chitosan, carrageenan, alginate, hyaluronic acid, dextran, poly(anhydrides), polyorthoesters, poly(vinyl alcohol), polyethylene glycol), poly (acrylic acid), and poly(ethylene oxide)-poly(propylene oxide)-poly(ethylene oxide) copolymer,
the method comprising:
a. introducing the biocompatible polymer solution into a thermally insulated container with a thermally conducting surface;
b. optionally allowing at least part of the biocompatible polymer solution to form a gel, by cooling the container in a cooling device to a temperature in the range of from biocompatible polymer solution melting point (Tm) to 25° C. thereby obtaining a biocompatible polymer gel/solution;

c. freezing the biocompatible gel solution or the biocompatible polymer gel/solution in a controlled fashion via the thermally conducting surface by, consecutively in the following order:
  (i) rapidly dropping the temperature of the cooling device to between about −10° C. and about −50° C., within no more than 5 minutes, so as to form a thin layer of frozen biocompatible polymer gel/solution on the thermally conducting surface;
  (ii) rapidly raising the temperature of the cooling device, within no more than 5 minutes, to a temperature closer to but still below the biocompatible polymer solution Tm;
  (iii) gradually lowering the temperature of the cooling device so as to induce a constant unidirectional growth rate of ice-crystals in the biocompatible polymer gel/solution, initiated from the frozen thin layer formed in step c (i); and
d. freeze drying the product of step c (iii).

2. A method as claimed in claim 1 wherein the porous material is a porous tissue scaffold.

3. A method as claimed in claim 1 wherein after freeze drying the material which corresponds to the thin layer formed in step c (i), and which has no columnar pores, is removed.

4. A method as claimed in claim 1 wherein after freeze drying the porous material is cross-linked.

5. A method as claimed in claim 4 wherein the porous material is cross-linked by a process which comprises chemical cross-linking.

6. A method as claimed in claim 4 wherein the porous material is cross-linked by a process which comprises dehydrothermal cross-linking.

7. A method as claimed in claim 1 wherein the biocompatible polymer solution is degassed before use.

8. A method as claimed in claim 1 wherein the biocompatible polymer solution is particle free.

9. A method as claimed in claim 1 wherein the biocompatible polymer solution is filter sterilized before use.

10. A method as claimed in claim 1 wherein the biocompatible polymer solution comprises a recombinant gelatin-like protein.

11. A method as claimed in claim 10 wherein the recombinant gelatin-like protein comprises at least one Arg-Gly-Asp-motif.

12. A method as claimed in claim 10 where in the recombinant gelatin-like protein the percentage of RGD-motifs related to the total number of amino acids is at least 0.4% and when said recombinant gelatin-like protein comprises 350 amino acids or more, the protein contains at least one RGD-motif per 350 amino acids.

13. A method as claimed in claim 10 where in the recombinant gelatin-like protein the percentage of RGD-motifs related to the total number of amino acids is at least 0.6%.

14. A method as claimed in claim 1 which provides a method for preparing a porous tissue scaffold material comprising the following steps:
  a. dissolution of the biocompatible polymer selected from the group consisting of collagen, gelatin, chitosan, carrageenan, alginate, hyaluronic acid, dextran, poly (anhydrides), polyorthoesters, poly(vinyl alcohol), polyethylene glycol), poly(acrylic acid), and poly(ethylene oxide)-poly(propylene oxide)-poly(ethylene oxide) copolymer in a solvent or solvent mixture;
  b. degassing of the biocompatible polymer solution;
  c. introducing the biocompatible polymer solution into a thermally insulated container with a single thermally conducting surface, optionally adding additives;
  d. optionally allowing at least part of the biocompatible polymer solution to gel by cooling the container to a temperature in the range of from biocompatible polymer solution Tm to 25° C.;
  e. unidirectionally freezing the biocompatible polymer solution with control of the freezing rate by exposing the container to a cooling device which utilizes a temperature profile comprising at least three steps, consecutively in the following order:
    (i) rapidly dropping the temperature of the cooling device to between about −10° C. and about −50° C., within no more than 5 minutes, so as to form a thin layer of frozen biocompatible polymer gel/solution on the thermally conducting surface;
    (ii) rapidly raising the temperature of the cooling device, within no more than 5 minutes, to a temperature closer to but still below biocompatible polymer solution Tm;
    (iii) gradually lowering the temperature of the cooling device so as to induce a laminar growth of ice-crystals in the biocompatible polymer gel/solution, initiated from the frozen layer formed in step e (i);
  f. freeze drying the material obtained in step (e) at reduced pressure;
  g. optionally removing the material which corresponds to the thin frozen layer formed in step e (i) and which has no columnar pores; and
  h. optionally cross-linking the material obtained in step g.

15. The method of claim 14, wherein the biocompatible polymer is selected from a group consisting of collagen, gelatin, chitosan, carrageenan, alginate, hyaluronic acid, dextran, poly(vinyl alcohol), poly(ethylene glycol), and poly (acrylic acid).

16. A porous material obtained by a method as described in claim 1.

17. The porous material as claimed in claim 16 which is a porous tissue scaffold.

18. The method of claim 1, wherein the biocompatible polymer is selected from a group consisting of collagen, gelatin, chitosan, carrageenan, alginate, hyaluronic acid, dextran, poly(vinyl alcohol), poly(ethylene glycol), and poly (acrylic acid).

* * * * *